US007829524B2

(12) United States Patent
Segura et al.

(10) Patent No.: US 7,829,524 B2
(45) Date of Patent: Nov. 9, 2010

(54) ANTIMICROBIAL PEPTIDES

(75) Inventors: Dorotea Raventos Segura, Humlebaek (DK); Per Holse Mygind, Soeborg (DK); Hans-Henrik Kristensen Hoegenhaug, Holte (DK); Alessandro Tossi, Gorizia (IT)

(73) Assignee: Novozymes Adenium Biotech A/S, Bagsvaerd (DK)

( * ) Notice: Subject to any disclaimer, the term of this patent is extended or adjusted under 35 U.S.C. 154(b) by 1289 days.

(21) Appl. No.: 10/560,260

(22) PCT Filed: Jun. 10, 2004

(86) PCT No.: PCT/DK2004/000400

§ 371 (c)(1),
(2), (4) Date: Dec. 9, 2005

(87) PCT Pub. No.: WO2004/108752

PCT Pub. Date: Dec. 16, 2004

(65) Prior Publication Data

US 2008/0213430 A1    Sep. 4, 2008

Related U.S. Application Data

(60) Provisional application No. 60/483,266, filed on Jun. 27, 2003.

(30) Foreign Application Priority Data

Jun. 11, 2003    (DK)    ................... 2003 00865

(51) Int. Cl.
*C07K 14/00*    (2006.01)
*A61K 38/16*    (2006.01)
(52) U.S. Cl. .................. 514/2; 514/12; 514/13; 530/324; 530/326; 424/9.1; 536/23.1
(58) Field of Classification Search .................... 514/2, 514/12, 13; 530/324, 326; 424/9.1; 536/23.1
See application file for complete search history.

(56) References Cited

FOREIGN PATENT DOCUMENTS

| WO | WO 96/09322 | 3/1996 |
|---|---|---|
| WO | WO 01/12668 | 2/2001 |

OTHER PUBLICATIONS

Tossi et al., FEBS Letters, vol. 339, pp. 108-112, (1994).
Tossi et al., Biopolymers, New York, NY, US, vol. 55, No. 1, pp. 4-30, (2000).
Tossi et al., European Journal of Biochemistry, Berlin, DE, vol. 250, No. 2, pp. 1997-12 (Dec. 1997).
Giangaspero et al., Eur. J. Biochem, vol. 268, pp. 5589-5600 (2001).
Pacor et al., Journal of Antimicrobial Chemotherapy vol. 50, pp. 339-348 (2002).
Tiozzo et al., Biochemical and Biophysical Research Communications, vol. 249, pp. 202-206 (1998).

*Primary Examiner*—Chih-Min Kam
(74) *Attorney, Agent, or Firm*—Elias J. Lambiris

(57) ABSTRACT

The present invention relates to polypeptides having antimicrobial activity and polynucleotides having a nucleotide sequence which encodes for the polypeptides. The invention also relates to nucleic acid constructs, vectors, and host cells comprising the nucleic acid constructs as well as methods for producing and using the polypeptides.

46 Claims, No Drawings

SEQUENCE LISTING

```
<160> NUMBER OF SEQ ID NOS: 75

<210> SEQ ID NO 1
<211> LENGTH: 29
<212> TYPE: PRT
<213> ORGANISM: Artificial
<220> FEATURE:
<223> OTHER INFORMATION: Synthetic antimicrobial peptide
<220> FEATURE:
<221> NAME/KEY: MISC_FEATURE
<222> LOCATION: (2)..(2)
<223> OTHER INFORMATION: Xaa = leucine or arginine
<220> FEATURE:
<221> NAME/KEY: MISC_FEATURE
<222> LOCATION: (3)..(3)
<223> OTHER INFORMATION: Xaa = leucine, isoleucine, valine or
      phenylalanine
<220> FEATURE:
<221> NAME/KEY: MISC_FEATURE
<222> LOCATION: (4)..(4)
<223> OTHER INFORMATION: Xaa = arginine or lysine
<220> FEATURE:
<221> NAME/KEY: MISC_FEATURE
<222> LOCATION: (6)..(6)
<223> OTHER INFORMATION: Xaa = leucine, isoleucine, valine or
      phenylalanine
<220> FEATURE:
<221> NAME/KEY: MISC_FEATURE
<222> LOCATION: (7)..(7)
<223> OTHER INFORMATION: Xaa = arginine, lysine, tryptophan or glycine
<220> FEATURE:
<221> NAME/KEY: MISC_FEATURE
<222> LOCATION: (8)..(8)
<223> OTHER INFORMATION: Xaa = lysine, arginine, glycine, methionine,
      asparagine or glutamic acid
<220> FEATURE:
<221> NAME/KEY: MISC_FEATURE
<222> LOCATION: (11)..(11)
<223> OTHER INFORMATION: Xaa = glycine, lysine, arginine or glutamic
      acid
<220> FEATURE:
<221> NAME/KEY: MISC_FEATURE
<222> LOCATION: (12)..(12)
<223> OTHER INFORMATION: Xaa = lysine, arginine, glycine or glutamic
      acid
<220> FEATURE:
<221> NAME/KEY: MISC_FEATURE
<222> LOCATION: (14)..(14)
<223> OTHER INFORMATION: Xaa = leucine or phenylalanine
<220> FEATURE:
```

```
<221> NAME/KEY: MISC_FEATURE
<222> LOCATION: (15)..(15)
<223> OTHER INFORMATION: Xaa = lycine or arginine
<220> FEATURE:
<221> NAME/KEY: MISC_FEATURE
<222> LOCATION: (17)..(17)
<223> OTHER INFORMATION: Xaa = leucine, isoleucine, phenylalanine,
      cysteine or tyrosine
<220> FEATURE:
<221> NAME/KEY: MISC_FEATURE
<222> LOCATION: (18)..(18)
<223> OTHER INFORMATION: Xaa = glycine, alanine or threonine
<220> FEATURE:
<221> NAME/KEY: MISC_FEATURE
<222> LOCATION: (19)..(19)
<223> OTHER INFORMATION: Xaa = glutamine, arginine, leucine or proline
<220> FEATURE:
<221> NAME/KEY: MISC_FEATURE
<222> LOCATION: (20)..(20)
<223> OTHER INFORMATION: Xaa = lysine, leucine, isoleucine, methionine
      or valine
<220> FEATURE:
<221> NAME/KEY: MISC_FEATURE
<222> LOCATION: (23)..(23)
<223> OTHER INFORMATION: Xaa = proline, alanine, histidine, asparagine
      or aspartic acid
<220> FEATURE:
<221> NAME/KEY: MISC_FEATURE
<222> LOCATION: (24)..(24)
<223> OTHER INFORMATION: Xaa = isoleucine or leucine
<220> FEATURE:
<221> NAME/KEY: MISC_FEATURE
<222> LOCATION: (25)..(25)
<223> OTHER INFORMATION: Xaa = arginine, histidine, glutamine or proline
<220> FEATURE:
<221> NAME/KEY: MISC_FEATURE
<222> LOCATION: (26)..(26)
<223> OTHER INFORMATION: Xaa = isoleucine or lysine

<400> SEQUENCE: 1

Gly Xaa Xaa Xaa Arg Xaa Xaa Xaa Lys Ile Xaa Xaa Lys Xaa Xaa Lys
1               5                   10                  15

Xaa Xaa Xaa Xaa Ile Lys Xaa Xaa Xaa Xaa Leu Val Pro
            20                  25

<210> SEQ ID NO 2
<211> LENGTH: 29
<212> TYPE: PRT
<213> ORGANISM: Artificial
<220> FEATURE:
<223> OTHER INFORMATION: Synthetic antimicrobial peptide
<220> FEATURE:
<221> NAME/KEY: MISC_FEATURE
<222> LOCATION: (2)..(2)
<223> OTHER INFORMATION: Xaa = leucine or arginine
<220> FEATURE:
<221> NAME/KEY: MISC_FEATURE
<222> LOCATION: (3)..(3)
<223> OTHER INFORMATION: Xaa = leucine, isoleucine, valine or
      phenylalanine
<220> FEATURE:
<221> NAME/KEY: MISC_FEATURE
<222> LOCATION: (4)..(4)
<223> OTHER INFORMATION: Xaa = arginine or lysine
<220> FEATURE:
<221> NAME/KEY: MISC_FEATURE
<222> LOCATION: (6)..(6)
<223> OTHER INFORMATION: Xaa = leucine, isoleucine, valine or
      phenylalanine
<220> FEATURE:
<221> NAME/KEY: MISC_FEATURE
<222> LOCATION: (7)..(7)
<223> OTHER INFORMATION: Xaa = arginine, tryptophane or glycine
<220> FEATURE:
<221> NAME/KEY: MISC_FEATURE
<222> LOCATION: (8)..(8)
```

```
<223> OTHER INFORMATION: Xaa = lysine, arginine, glycine, methionine,
      asparagine or glutamic acid
<220> FEATURE:
<221> NAME/KEY: MISC_FEATURE
<222> LOCATION: (11)..(11)
<223> OTHER INFORMATION: Xaa = glycine, lysine, arginine or glutamic
      acid
<220> FEATURE:
<221> NAME/KEY: MISC_FEATURE
<222> LOCATION: (12)..(12)
<223> OTHER INFORMATION: Xaa = lysine, arginine, glycine or glutamic
      acid
<220> FEATURE:
<221> NAME/KEY: MISC_FEATURE
<222> LOCATION: (14)..(14)
<223> OTHER INFORMATION: Xaa = leucine or phenylalanine
<220> FEATURE:
<221> NAME/KEY: MISC_FEATURE
<222> LOCATION: (17)..(17)
<223> OTHER INFORMATION: Xaa = isoleucine, phenylalanine, cysteine or
      tyrosine
<220> FEATURE:
<221> NAME/KEY: MISC_FEATURE
<222> LOCATION: (19)..(19)
<223> OTHER INFORMATION: Xaa = glutamine, leucine or proline
<220> FEATURE:
<221> NAME/KEY: MISC_FEATURE
<222> LOCATION: (20)..(20)
<223> OTHER INFORMATION: Xaa = lysine, leucine, isoleucine, methionine
      or valine
<220> FEATURE:
<221> NAME/KEY: MISC_FEATURE
<222> LOCATION: (23)..(23)
<223> OTHER INFORMATION: Xaa = proline, alanine, histidine, asparagine
      or aspartic acid
<220> FEATURE:
<221> NAME/KEY: MISC_FEATURE
<222> LOCATION: (24)..(24)
<223> OTHER INFORMATION: Xaa = isoleucine or leucine
<220> FEATURE:
<221> NAME/KEY: MISC_FEATURE
<222> LOCATION: (25)..(25)
<223> OTHER INFORMATION: Xaa = arginine, histidine, glutamine or proline
<220> FEATURE:
<221> NAME/KEY: MISC_FEATURE
<222> LOCATION: (26)..(26)
<223> OTHER INFORMATION: Xaa = isoleucine or lysine

<400> SEQUENCE: 2

Gly Xaa Xaa Xaa Arg Xaa Xaa Xaa Lys Ile Xaa Xaa Lys Xaa Lys Lys
1               5                   10                  15

Xaa Gly Xaa Xaa Ile Lys Xaa Xaa Xaa Xaa Leu Val Pro
            20                  25

<210> SEQ ID NO 3
<211> LENGTH: 29
<212> TYPE: PRT
<213> ORGANISM: Artificial
<220> FEATURE:
<223> OTHER INFORMATION: Synthetic antimicrobial peptide (Cat1)

<400> SEQUENCE: 3

Gly Leu Leu Arg Arg Leu Arg Lys Lys Ile Gly Lys Lys Leu Lys Lys
1               5                   10                  15

Ile Gly Gln Lys Ile Lys Pro Ile Arg Ile Leu Val Pro
            20                  25

<210> SEQ ID NO 4
<211> LENGTH: 29
<212> TYPE: PRT
<213> ORGANISM: Artificial
<220> FEATURE:
<223> OTHER INFORMATION: Synthetic antimicrobial peptide
```

<400> SEQUENCE: 4

Gly Leu Leu Arg Arg Leu Arg Gly Lys Ile Gly Lys Lys Leu Lys Lys
1               5                   10                  15

Ile Gly Gln Lys Ile Lys Ala Ile Arg Lys Leu Val Pro
            20                  25

<210> SEQ ID NO 5
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 5

Gly Leu Leu Arg Arg Phe Arg Lys Lys Ile Gly Gly Lys Leu Lys Lys
1               5                   10                  15

Tyr Gly Gln Ile Ile Lys His Leu Arg Ile Leu Val Pro
            20                  25

<210> SEQ ID NO 6
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 6

Gly Leu Leu Arg Arg Leu Arg Arg Lys Ile Gly Gly Lys Leu Lys Lys
1               5                   10                  15

Phe Gly Gln Lys Ile Lys Pro Leu Arg Lys Leu Val Pro
            20                  25

<210> SEQ ID NO 7
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 7

Gly Leu Leu Arg Arg Leu Arg Lys Lys Ile Gly Lys Lys Leu Lys Lys
1               5                   10                  15

Phe Gly Gln Lys Ile Lys His Ile Arg Ile Leu Val Pro
            20                  25

<210> SEQ ID NO 8
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 8

Gly Leu Leu Lys Arg Leu Gly Arg Lys Ile Gly Lys Lys Leu Lys Lys
1               5                   10                  15

Phe Gly Gln Lys Ile Lys Ala Ile Arg Lys Leu Val Pro
            20                  25

<210> SEQ ID NO 9
<211> LENGTH: 29
<212> TYPE: PRT
<213> ORGANISM: Artificial
<220> FEATURE:

<223> OTHER INFORMATION: Synthetic antimicrobial peptide

<400> SEQUENCE: 9

Gly Arg Phe Lys Arg Phe Trp Lys Lys Ile Gly Arg Lys Phe Lys Lys
1               5                   10                  15
Ile Gly Gln Met Leu Lys Pro Ile Arg Ile Leu Val Pro
            20                  25

<210> SEQ ID NO 10
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 10

Gly Leu Leu Lys Arg Leu Arg Lys Lys Ile Gly Lys Lys Leu Lys Lys
1               5                   10                  15
Ile Gly Pro Lys Ile Lys His Ile Arg Lys Leu Val Pro
            20                  25

<210> SEQ ID NO 11
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 11

Gly Leu Leu Arg Arg Phe Trp Met Lys Ile Gly Gly Lys Leu Lys Lys
1               5                   10                  15
Phe Gly Gln Met Ile Lys His Leu Arg Lys Leu Val Pro
            20                  25

<210> SEQ ID NO 12
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 12

Gly Arg Leu Arg Arg Leu Arg Arg Lys Ile Gly Glu Lys Leu Lys Lys
1               5                   10                  15
Phe Gly Gln Val Ile Lys Ala Leu Arg Ile Leu Val Pro
            20                  25

<210> SEQ ID NO 13
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 13

Gly Leu Leu Arg Arg Leu Trp Arg Lys Ile Gly Arg Lys Leu Lys Lys
1               5                   10                  15
Tyr Gly Gln Lys Ile Lys Ala Leu Arg Lys Leu Val Pro
            20                  25

<210> SEQ ID NO 14
<211> LENGTH: 29
<212> TYPE: PRT
<213> ORGANISM: Artificial

-continued

```
<220> FEATURE:
<223> OTHER INFORMATION: Synthetic antimicrobial peptide

<400> SEQUENCE: 14

Gly Arg Phe Arg Arg Phe Arg Lys Lys Ile Gly Lys Lys Leu Lys Lys
1               5                   10                  15

Ile Gly Leu Val Ile Lys His Ile Arg Ile Leu Val Pro
            20                  25

<210> SEQ ID NO 15
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 15

Gly Leu Leu Arg Arg Leu Arg Arg Lys Ile Gly Lys Lys Leu Lys Lys
1               5                   10                  15

Phe Gly Gln Lys Ile Lys His Ile Arg Ile Leu Val Pro
            20                  25

<210> SEQ ID NO 16
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 16

Gly Leu Leu Arg Arg Leu Arg Asn Lys Ile Arg Lys Lys Leu Lys Lys
1               5                   10                  15

Phe Gly Gln Lys Ile Lys Ala Ile Arg Ile Leu Val Pro
            20                  25

<210> SEQ ID NO 17
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 17

Gly Leu Arg Arg Leu Trp Arg Lys Ile Gly Arg Lys Leu Lys Lys
1               5                   10                  15

Tyr Gly Gln Val Ile Lys His Leu Arg Ile Leu Val Pro
            20                  25

<210> SEQ ID NO 18
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 18

Gly Leu Phe Lys Arg Leu Arg Lys Lys Ile Gly Lys Lys Leu Lys Lys
1               5                   10                  15

Phe Gly Gln Lys Ile Lys Pro Leu Arg Lys Leu Val Pro
            20                  25

<210> SEQ ID NO 19
<211> LENGTH: 29
<212> TYPE: PRT
```

```
<213> ORGANISM: Artificial
<220> FEATURE:
<223> OTHER INFORMATION: Synthetic antimicrobial peptide

<400> SEQUENCE: 19

Gly Leu Leu Arg Arg Phe Gly Arg Lys Ile Gly Lys Lys Phe Lys Lys
1               5                   10                  15

Phe Gly Pro Lys Ile Lys His Leu Arg Lys Leu Val Pro
            20                  25

<210> SEQ ID NO 20
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 20

Gly Leu Phe Arg Arg Phe Arg Arg Lys Ile Gly Lys Lys Leu Lys Lys
1               5                   10                  15

Phe Gly Gln Lys Ile Lys Pro Leu Arg Lys Leu Val Pro
            20                  25

<210> SEQ ID NO 21
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 21

Gly Leu Leu Arg Arg Phe Arg Arg Lys Ile Gly Arg Lys Leu Lys Lys
1               5                   10                  15

Tyr Gly Leu Met Ile Lys Pro Leu Arg Lys Leu Val Pro
            20                  25

<210> SEQ ID NO 22
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 22

Gly Leu Leu Lys Arg Phe Arg Gly Lys Ile Gly Lys Lys Leu Lys Lys
1               5                   10                  15

Tyr Gly Gln Leu Ile Lys Ala Ile Arg Ile Leu Val Pro
            20                  25

<210> SEQ ID NO 23
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 23

Gly Leu Phe Arg Arg Leu Arg Lys Lys Ile Gly Lys Lys Leu Lys Lys
1               5                   10                  15

Ile Gly Gln Leu Ile Lys Ala Ile Arg Ile Leu Val Pro
            20                  25

<210> SEQ ID NO 24
<211> LENGTH: 29
```

```
<212> TYPE: PRT
<213> ORGANISM: Artificial
<220> FEATURE:
<223> OTHER INFORMATION: Synthetic antimicrobial peptide

<400> SEQUENCE: 24

Gly Leu Leu Arg Arg Phe Gly Lys Lys Ile Gly Lys Lys Phe Lys Lys
1               5                   10                  15

Tyr Gly Gln Lys Ile Lys Asn Leu Arg Ile Leu Val Pro
            20                  25

<210> SEQ ID NO 25
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 25

Gly Leu Leu Lys Arg Leu Arg Lys Lys Ile Gly Lys Lys Leu Lys Lys
1               5                   10                  15

Ile Gly Gln Lys Ile Lys Pro Ile Arg Lys Leu Val Pro
            20                  25

<210> SEQ ID NO 26
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 26

Gly Leu Leu Arg Arg Phe Gly Arg Lys Ile Gly Lys Lys Phe Lys Lys
1               5                   10                  15

Phe Gly Pro Lys Ile Lys His Leu Arg Lys Leu Val Pro
            20                  25

<210> SEQ ID NO 27
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 27

Gly Arg Leu Arg Arg Leu Arg Arg Lys Ile Arg Lys Lys Leu Lys Lys
1               5                   10                  15

Tyr Gly Gln Lys Ile Lys Ala Ile Arg Lys Leu Val Pro
            20                  25

<210> SEQ ID NO 28
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 28

Gly Arg Phe Arg Arg Phe Arg Lys Lys Ile Gly Gly Lys Leu Lys Lys
1               5                   10                  15

Ile Gly Gln Val Ile Lys Asp Ile Arg Ile Leu Val Pro
            20                  25

<210> SEQ ID NO 29
```

```
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 29

Gly Arg Phe Arg Arg Phe Arg Lys Lys Ile Gly Lys Lys Phe Lys Lys
1               5                   10                  15

Phe Gly Gln Met Ile Lys Ala Leu Arg Ile Leu Val Pro
            20                  25

<210> SEQ ID NO 30
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 30

Gly Arg Leu Arg Arg Phe Arg Lys Lys Ile Gly Lys Lys Leu Lys Lys
1               5                   10                  15

Ile Gly Gln Met Ile Lys His Ile Arg Ile Leu Val Pro
            20                  25

<210> SEQ ID NO 31
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 31

Gly Leu Val Arg Arg Phe Arg Arg Lys Ile Gly Lys Lys Leu Lys Lys
1               5                   10                  15

Ile Gly Gln Ile Ile Lys Ala Ile Arg Lys Leu Val Pro
            20                  25

<210> SEQ ID NO 32
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 32

Gly Leu Leu Arg Arg Leu Arg Arg Lys Ile Gly Lys Lys Phe Lys Lys
1               5                   10                  15

Ile Gly Gln Val Ile Lys His Leu Arg Lys Leu Val Pro
            20                  25

<210> SEQ ID NO 33
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 33

Gly Leu Phe Arg Arg Leu Arg Gly Lys Ile Gly Lys Lys Leu Lys Lys
1               5                   10                  15

Ile Gly Gln Lys Ile Lys Ala Ile Arg Ile Leu Val Pro
            20                  25
```

<210> SEQ ID NO 34
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 34

Gly Leu Phe Arg Arg Leu Gly Lys Lys Ile Gly Lys Lys Leu Lys Lys
1               5                   10                  15

Phe Gly Gln Val Ile Lys His Ile Arg Ile Leu Val Pro
            20                  25

<210> SEQ ID NO 35
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 35

Gly Leu Leu Arg Arg Leu Gly Lys Lys Ile Gly Lys Lys Phe Lys Lys
1               5                   10                  15

Phe Gly Gln Val Ile Lys Ala Leu Arg Ile Leu Val Pro
            20                  25

<210> SEQ ID NO 36
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 36

Gly Leu Phe Arg Arg Leu Gly Arg Lys Ile Gly Lys Lys Leu Lys Lys
1               5                   10                  15

Ile Gly Gln Val Ile Lys His Ile Arg Ile Leu Val Pro
            20                  25

<210> SEQ ID NO 37
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 37

Gly Leu Leu Arg Arg Leu Arg Lys Lys Ile Glu Lys Lys Leu Lys Lys
1               5                   10                  15

Tyr Gly Pro Lys Ile Lys Ala Leu Arg Lys Leu Val Pro
            20                  25

<210> SEQ ID NO 38
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 38

Gly Arg Ile Lys Arg Val Gly Glu Lys Ile Gly Lys Lys Leu Lys Lys
1               5                   10                  15

Ile Gly Gln Val Ile Lys His Leu Arg Ile Leu Val Pro
            20                  25

```
<210> SEQ ID NO 39
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 39

Gly Leu Phe Arg Arg Phe Gly Lys Lys Ile Gly Lys Lys Leu Lys Lys
1               5                   10                  15

Ile Gly Gln Val Ile Lys Ala Leu Arg Ile Leu Val Pro
            20                  25

<210> SEQ ID NO 40
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 40

Gly Arg Leu Arg Arg Phe Gly Lys Lys Ile Gly Lys Lys Leu Lys Lys
1               5                   10                  15

Phe Gly Gln Leu Ile Lys Ala Leu Arg Ile Leu Val Pro
            20                  25

<210> SEQ ID NO 41
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 41

Gly Leu Leu Arg Arg Phe Trp Lys Lys Ile Gly Lys Lys Leu Lys Lys
1               5                   10                  15

Phe Gly Gln Lys Ile Lys Pro Leu Pro Lys Leu Val Pro
            20                  25

<210> SEQ ID NO 42
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 42

Gly Arg Phe Arg Arg Leu Gly Arg Lys Ile Gly Glu Lys Leu Lys Lys
1               5                   10                  15

Phe Gly Gln Val Ile Lys Ala Ile Arg Ile Leu Val Pro
            20                  25

<210> SEQ ID NO 43
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 43

Gly Leu Phe Arg Arg Phe Gly Lys Lys Ile Gly Lys Lys Leu Lys Lys
1               5                   10                  15

Ile Gly Gln Lys Ile Lys Pro Ile His Lys Leu Val Pro
            20                  25
```

<210> SEQ ID NO 44
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 44

Gly Leu Leu Lys Arg Leu Arg Lys Lys Ile Gly Lys Lys Leu Lys Lys
1               5                   10                  15

Ile Gly Gln Met Ile Lys His Ile Arg Ile Leu Val Pro
            20                  25

<210> SEQ ID NO 45
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 45

Gly Leu Leu Arg Arg Phe Arg Glu Lys Ile Gly Lys Lys Leu Lys Lys
1               5                   10                  15

Tyr Gly Gln Lys Ile Lys His Leu Arg Lys Leu Val Pro
            20                  25

<210> SEQ ID NO 46
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 46

Gly Leu Phe Arg Arg Leu Arg Arg Lys Ile Gly Lys Lys Phe Lys Lys
1               5                   10                  15

Phe Gly Gln Lys Ile Lys Pro Leu Arg Lys Leu Val Pro
            20                  25

<210> SEQ ID NO 47
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 47

Gly Leu Phe Arg Arg Phe Trp Lys Lys Ile Gly Arg Lys Leu Lys Lys
1               5                   10                  15

Ile Gly Gln Lys Ile Lys Pro Leu Gln Ile Leu Val Pro
            20                  25

<210> SEQ ID NO 48
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 48

Gly Leu Leu Arg Arg Leu Trp Lys Lys Ile Gly Arg Lys Phe Lys Lys
1               5                   10                  15

Tyr Gly Gln Val Ile Lys His Ile Arg Lys Leu Val Pro

```
                20                  25

<210> SEQ ID NO 49
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 49

Gly Leu Leu Arg Arg Leu Gly Arg Lys Ile Gly Lys Lys Leu Lys Lys
1               5                   10                  15

Ile Gly Gln Lys Ile Lys Ala Ile Arg Ile Leu Val Pro
            20                  25

<210> SEQ ID NO 50
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 50

Gly Leu Leu Arg Arg Phe Arg Asn Lys Ile Gly Lys Lys Leu Lys Lys
1               5                   10                  15

Ile Gly Gln Lys Ile Lys Pro Ile Arg Lys Leu Val Pro
            20                  25

<210> SEQ ID NO 51
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 51

Gly Arg Phe Lys Arg Leu Arg Lys Lys Ile Gly Lys Lys Phe Lys Lys
1               5                   10                  15

Ile Gly Gln Lys Ile Lys Asp Ile Arg Lys Leu Val Pro
            20                  25

<210> SEQ ID NO 52
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 52

Gly Leu Phe Arg Arg Ile Arg Arg Lys Ile Gly Lys Lys Phe Lys Lys
1               5                   10                  15

Phe Gly Gln Val Ile Lys Pro Leu Arg Lys Leu Val Pro
            20                  25

<210> SEQ ID NO 53
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 53

Gly Arg Leu Arg Arg Leu Gly Lys Lys Ile Gly Glu Lys Leu Lys Lys
1               5                   10                  15
```

```
Phe Gly Gln Met Ile Lys His Ile Arg Ile Leu Val Pro
            20                  25
```

```
<210> SEQ ID NO 54
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 54

Gly Leu Leu Arg Arg Leu Gly Lys Ile Gly Lys Lys Phe Lys Lys
1               5                   10                  15

Cys Gly Gln Val Ile Lys Ala Ile Arg Ile Leu Val Pro
            20                  25
```

```
<210> SEQ ID NO 55
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 55

Gly Leu Leu Arg Arg Phe Arg Lys Lys Ile Gly Glu Lys Phe Lys Lys
1               5                   10                  15

Phe Gly Gln Lys Ile Lys Asn Ile Arg Ile Leu Val Pro
            20                  25
```

```
<210> SEQ ID NO 56
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 56

Gly Leu Leu Arg Arg Leu Arg Lys Lys Ile Gly Lys Lys Leu Lys Lys
1               5                   10                  15

Ile Gly Gln Lys Ile Lys Pro Ile Arg Lys Leu Val Pro
            20                  25
```

```
<210> SEQ ID NO 57
<211> LENGTH: 29
<212> TYPE: PRT
<213> ORGANISM: Artificial
<220> FEATURE:
<223> OTHER INFORMATION: Synthetic antimicrobial peptide

<400> SEQUENCE: 57

Gly Leu Leu Arg Arg Phe Arg Lys Lys Ile Gly Lys Lys Leu Lys Lys
1               5                   10                  15

Tyr Gly Gln Lys Ile Lys His Leu Arg Ile Leu Val Pro
            20                  25
```

```
<210> SEQ ID NO 58
<211> LENGTH: 19
<212> TYPE: PRT
<213> ORGANISM: Artificial
<220> FEATURE:
<223> OTHER INFORMATION: Synthetic antimicrobial peptide
<220> FEATURE:
<221> NAME/KEY: MISC_FEATURE
<222> LOCATION: (2)..(2)
<223> OTHER INFORMATION: Xaa = leucine or arginine
<220> FEATURE:
```

```
<221> NAME/KEY: MISC_FEATURE
<222> LOCATION: (3)..(3)
<223> OTHER INFORMATION: Xaa = leucine or phenylalanine
<220> FEATURE:
<221> NAME/KEY: MISC_FEATURE
<222> LOCATION: (4)..(4)
<223> OTHER INFORMATION: Xaa = arginine or lysine
<220> FEATURE:
<221> NAME/KEY: MISC_FEATURE
<222> LOCATION: (6)..(6)
<223> OTHER INFORMATION: Xaa = leucine or phenylalanine
<220> FEATURE:
<221> NAME/KEY: MISC_FEATURE
<222> LOCATION: (7)..(7)
<223> OTHER INFORMATION: Xaa = arginine, lysine or glycine
<220> FEATURE:
<221> NAME/KEY: MISC_FEATURE
<222> LOCATION: (8)..(8)
<223> OTHER INFORMATION: Xaa = arginine, lysine or glutamic acid
<220> FEATURE:
<221> NAME/KEY: MISC_FEATURE
<222> LOCATION: (11)..(11)
<223> OTHER INFORMATION: Xaa = glycine or lysine
<220> FEATURE:
<221> NAME/KEY: MISC_FEATURE
<222> LOCATION: (12)..(12)
<223> OTHER INFORMATION: Xaa = lysine, arginine or glutamic acid
<220> FEATURE:
<221> NAME/KEY: MISC_FEATURE
<222> LOCATION: (14)..(14)
<223> OTHER INFORMATION: Xaa = leucine or phenylalanine
<220> FEATURE:
<221> NAME/KEY: MISC_FEATURE
<222> LOCATION: (15)..(15)
<223> OTHER INFORMATION: Xaa = lysine or arginine
<220> FEATURE:
<221> NAME/KEY: MISC_FEATURE
<222> LOCATION: (17)..(17)
<223> OTHER INFORMATION: Xaa = isoleucine or leucine
<220> FEATURE:
<221> NAME/KEY: MISC_FEATURE
<222> LOCATION: (18)..(18)
<223> OTHER INFORMATION: Xaa = alanine or threonine

<400> SEQUENCE: 58

Gly Xaa Xaa Xaa Arg Xaa Xaa Xaa Lys Ile Xaa Xaa Lys Xaa Xaa Lys
1               5                   10                  15

Xaa Xaa Arg

<210> SEQ ID NO 59
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 59

Gly Leu Leu Arg Arg Leu Arg Lys Lys Ile Gly Lys Lys Leu Lys Lys
1               5                   10                  15

Ile Ala Arg

<210> SEQ ID NO 60
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 60

Gly Leu Phe Arg Arg Leu Lys Arg Lys Ile Gly Arg Lys Phe Lys Lys
1               5                   10                  15
```

Ile Ala Arg

<210> SEQ ID NO 61
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 61

Gly Leu Leu Lys Arg Leu Gly Arg Lys Ile Gly Lys Lys Phe Lys Lys
1               5                   10                  15

Ile Ala Arg

<210> SEQ ID NO 62
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 62

Gly Leu Leu Arg Arg Phe Arg Lys Lys Ile Gly Lys Lys Leu Lys Lys
1               5                   10                  15

Ile Ala Arg

<210> SEQ ID NO 63
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 63

Gly Leu Leu Arg Arg Leu Arg Lys Lys Ile Gly Lys Lys Leu Lys Lys
1               5                   10                  15

Ile Thr Arg

<210> SEQ ID NO 64
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 64

Gly Leu Phe Arg Arg Leu Arg Lys Lys Ile Gly Lys Lys Leu Lys Lys
1               5                   10                  15

Ile Ala Arg

<210> SEQ ID NO 65
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 65

Gly Leu Phe Arg Arg Leu Lys Arg Lys Ile Gly Lys Lys Leu Lys Lys
1               5                   10                  15

Ile Ala Arg

<210> SEQ ID NO 66

-continued

<210> SEQ ID NO 66
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 66

Gly Leu Leu Lys Arg Leu Gly Arg Lys Ile Gly Lys Lys Leu Lys Lys
1               5                   10                  15

Ile Ala Arg

<210> SEQ ID NO 67
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 67

Gly Leu Leu Arg Arg Phe Arg Lys Lys Ile Gly Lys Lys Leu Lys Lys
1               5                   10                  15

Ile Thr Arg

<210> SEQ ID NO 68
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 68

Gly Leu Leu Arg Arg Leu Arg Lys Lys Ile Gly Arg Lys Phe Lys Lys
1               5                   10                  15

Ile Ala Arg

<210> SEQ ID NO 69
<211> LENGTH: 19
<212> TYPE: PRT
<213> ORGANISM: Artificial
<220> FEATURE:
<223> OTHER INFORMATION: Synthetic antimicrobial peptide

<400> SEQUENCE: 69

Gly Leu Phe Arg Arg Leu Arg Lys Lys Ile Gly Lys Lys Phe Lys Lys
1               5                   10                  15

Ile Ala Arg

<210> SEQ ID NO 70
<211> LENGTH: 90
<212> TYPE: DNA
<213> ORGANISM: Artificial
<220> FEATURE:
<223> OTHER INFORMATION: Synthetic Cat1 gene
<220> FEATURE:
<221> NAME/KEY: CDS
<222> LOCATION: (1)..(90)

<400> SEQUENCE: 70 ggc ctg ctg cgc cgt ctg cgc aag aag att ggc aaa aag ctg aag aaa    48
Gly Leu Leu Arg Arg Leu Arg Lys Lys Ile Gly Lys Lys Leu Lys Lys
1               5                   10                  15 att ggc cag aag att aaa ccg att cgc att ctg gtg ccg tag            90
Ile Gly Gln Lys Ile Lys Pro Ile Arg Ile Leu Val Pro
            20                  25

<210> SEQ ID NO 71
<211> LENGTH: 29
<212> TYPE: PRT
<213> ORGANISM: Artificial
<220> FEATURE:
<223> OTHER INFORMATION: Synthetic Construct

<400> SEQUENCE: 71

Gly Leu Leu Arg Arg Leu Arg Lys Lys Ile Gly Lys Lys Leu Lys Lys
1               5                   10                  15

Ile Gly Gln Lys Ile Lys Pro Ile Arg Ile Leu Val Pro
            20                  25

<210> SEQ ID NO 72
<211> LENGTH: 129
<212> TYPE: DNA
<213> ORGANISM: Artificial
<220> FEATURE:
<223> OTHER INFORMATION: Primer 1 sequence

<400> SEQUENCE: 72
attattcaga tgctggatcc ggcggaaggc ctgctgcgcc gtctgcgcaa gaagattggc      60
aaaaagctga agaaaattgg ccagaagatt aaaccgattc gcattctggt gccgtagctc     120
gagattatt                                                             129

<210> SEQ ID NO 73
<211> LENGTH: 129
<212> TYPE: DNA
<213> ORGANISM: Artificial
<220> FEATURE:
<223> OTHER INFORMATION: Primer 2 sequence

<400> SEQUENCE: 73
aataatctcg agctacggca ccagaatgcg aatcggttta atcttctggc caattttctt      60 cagcttttig ccaatcttct tgcgcagacg gcgcagcagg ccttccgccg gatccagcat    120
ctgaataat                                                             129

<210> SEQ ID NO 74
<211> LENGTH: 20
<212> TYPE: DNA
<213> ORGANISM: Artificial
<220> FEATURE:
<223> OTHER INFORMATION: Primer 3 sequence

<400> SEQUENCE: 74
tgctagttat tgctcagcgg                                                  20

<210> SEQ ID NO 75
<211> LENGTH: 19
<212> TYPE: DNA
<213> ORGANISM: Artificial
<220> FEATURE:
<223> OTHER INFORMATION: Primer 4 sequence

<400> SEQUENCE: 75
accgtagttg cgcccatcg                                                   19

ANTIMICROBIAL PEPTIDES

CROSS-REFERENCE TO RELATED APPLICATIONS

This application is a 35 U.S.C. 371 national application of PCT/DK2004/000400, filed Jun. 10, 2004, which claims priority or the benefit under 35 U.S.C. 119 of Danish application no. PA 2003 00865 filed Jun. 11, 2003 and U.S. provisional application No. 60/483,266 filed Jun. 27, 2003, the contents of which are fully incorporated herein by reference.

BACKGROUND

In recent years, the variety of antimicrobial agents has increased substantially, along with a parallel increase in resistant pathogenic microorganisms. Resistance is now recognized against all clinically available antimicrobial agents. The response to antimicrobial resistance in the medical community has been to use new or alternative antibiotics not previously used against the resistant bacteria. This approach has required the continuous development of new antibiotics, either as modifications of currently existing compounds or as combinations of compounds that may inhibit or bypass the bacterial resistance mechanisms.

It is an object of the present invention to provide new polypeptides having improved antimicrobial activity and polynucleotides encoding the polypeptides.

SUMMARY

In a first aspect the present invention relates to polypeptides having antimicrobial activity, comprising the amino acid sequence, or a fragment thereof of at least 19 amino acids having antimicrobial activity:

G-$X_1$-$X_2$-$X_3$-R-$X_4$-$X_5$-$X_6$-K-I-$X_7$-$X_8$-K-$X_9$-$X_{10}$-K-$X_{11}$-$X_{12}$-$X_{13}$-$X_{14}$-I-K-$X_{15}$-$X_{16}$-$X_{17}$-$X_{18}$-L-V-P (SEQ ID NO: 1);

wherein $X_1$ = L or R; $X_2$ = L, V, I or F; $X_3$ = R or K;
$X_4$ = L, V, I or F; $X_5$ = R, K, W or G; $X_6$ = K, R, G, M, N or E;
$X_7$ = G, R, K or E; $X_8$ = G, R, K or E; $X_9$ = L or F;
$X_{10}$ = K or R; $X_{11}$ = I, L, F, C or Y; $X_{12}$ = G, A or T;
$X_{13}$ = Q, R, L or P; $X_{14}$ = K, I, M, L or V; $X_{15}$ = P, A, H, N or D;
$X_{16}$ = I or L; $X_{17}$ = R, H, Q or P; $X_{18}$ = I or K.

In another aspect the invention relates to polypeptides having antimicrobial activity, comprising an amino acid sequence, which differs by at the most two amino acids from the amino acid sequence:

G-$X_1$-$X_2$-$X_3$-R-$X_4$-$X_5$-$X_6$-K-I-$X_7$-$X_8$-K-$X_9$-$X_{10}$-K-$X_{11}$-$X_{12}$-Z (amino acids 1-19 or 1-29 of SEQ ID NO: 1);

wherein $X_1$ = L or R; $X_2$ = L, V, I or F; $X_3$ = R or K;
$X_4$ = L, V, I or F; $X_5$ = R, K, W or G; $X_6$ = K, R, G, M, N or E;
$X_7$ = G, R, K or E; $X_8$ = G, R, K or E; $X_9$ = L or F;
$X_{10}$ = K or R; $X_{11}$ = I, L, F, C or Y; $X_{12}$ = G, A or T;
Z = R or $X_{13}$-$X_{14}$-I-K-$X_{15}$-$X_{16}$-$X_{17}$-$X_{18}$-V-P
(amino acids of 19-29 SEQ ID NO: 1);

wherein $X_{13}$ = Q, L or P; $X_{14}$ = K, I, M, L or V; $X_{15}$ = P, A, H, N or D;
$X_{16}$ = I or L; $X_{17}$ = R, H, Q or P; $X_{18}$ = I or K.

In a second aspect the present invention relates to polynucleotides having a nucleotide sequence which encodes for the polypeptide of the invention.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

In a fifth aspect the present invention relates to a recombinant host cell comprising the nucleic acid construct of the invention.

In a sixth aspect the present invention relates to a method for producing a polypeptide of the invention, the method comprising:

(a) cultivating a recombinant host cell of the invention under conditions conducive for production of the polypeptide; and (b) recovering the polypeptide.

Other aspects of the present invention will be apparent from the below description and from the appended claims.

Definitions

Before discussing the present invention in further details, the following terms and conventions will first be defined:

Antimicrobial activity: The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect and/or a virucidal effect, wherein the term "bactericidal" is to be understood as capable of killing bacterial cells. The term "bacteriostatic" is to be understood as capable of inhibiting bacterial growth, i.e. inhibiting growing bacterial cells. The term "fungicidal" is to be understood as capable of killing fungal cells. The term "fungistatic" is to be understood as capable of inhibiting fungal growth, i.e. inhibiting growing fungal cells. The term "virucidal" is to be understood as capable of inactivating virus. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

For purposes of the present invention, antimicrobial activity may be determined according to the procedure described by Lehrer et al., Journal of Immunological Methods, Vol. 137 (2) pp. 167-174 (1991).

Polypeptides having antimicrobial activity may be capable of reducing the number of living cells of *Escherichia coli* (DSM 1576) to ¹⁄₁₀₀ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Escherichia coli* (DSM 1576) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

Polypeptides having antimicrobial activity may be capable of reducing the number of living cells of *Bacillus subtilis* (ATCC 6633) to $\frac{1}{100}$ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The polypeptides of the present invention should preferably have at least 20% of the antimicrobial activity of the polypeptide consisting of the amino acid sequence shown as amino acids 1 to 29 of anyone of SEQ ID NO:1 to SEQ ID NO:57 or amino acids 1 to 19 of anyone of SEQ ID NO:58 to SEQ ID NO:69. In a particular preferred embodiment, the polypeptides should have at least 40%, such as at least 50%, preferably at least 60%, such as at least 70%, more preferably at least 80%, such as at least 90%, most preferably at least 95%, such as about or at least 100% of the antimicrobial activity of the polypeptide consisting of the amino acid sequence shown as amino acids 1 to 29 of anyone of SEQ ID NO:1 to SEQ ID NO:57 or amino acids 1 to 19 of anyone of SEQ ID NO:58 to SEQ ID NO:69.

Fragment: When used herein, a "fragment" of the amino acid sequence: G-$X_1$-$X_2$-$X_3$-R-$X_4$-$X_5$-$X_6$-K-I-$X_7$-$X_8$-K-$X_9$-$X_{10}$-K-$X_{11}$-$X_{12}$-Z (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}$-$X_{14}$-I-K-$X_{15}$-$X_{16}$-$X_{17}$-$X_{18}$-L-V-P (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or anyone of SEQ ID NO:1 to SEQ ID NO:57 or anyone of SEQ ID NO:58 to SEQ ID NO:69 is a subsequence of the polypeptides wherein one or more amino acids have been deleted from the amino and/or carboxyl terminus. Preferably the one or more amino acids have been deleted from the carboxyl terminus. A fragment may consist of at least 19 amino acids, such as 19, 20, 21, 22, 23, 24, 25, 26, 27, 28 or 29 amino acids. Preferably a fragment consists of at least 19 amino acids as counted from the amino terminus of the polypeptide.

Allelic variant: In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems. Thus, a substantially pure polynucleotide contains at the most 10% by weight of other polynucleotide material with which it is natively associated (lower percentages of other polynucleotide material are preferred, e.g. at the most 8% by weight, at the most 6% by weight, at the most 5% by weight, at the most 4% at the most 3% by weight, at the most 2% by weight, at the most 1% by weight, and at the most ½% by weight). A substantially pure polynucleotide may, however, include naturally occurring 5' and 3' untranslated regions, such as promoters and terminators. It is preferred that the substantially pure polynucleotide is at least 92% pure, i.e. that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99%, and at the most 99.5% pure. The polynucleotides disclosed herein are preferably in a substantially pure form. In particular, it is preferred that the polynucleotides disclosed herein are in "essentially pure form", i.e. that the polynucleotide preparation is essentially free of other polynucleotide material with which it is natively associated. Herein, the term "substantially pure polynucleotide" is synonymous with the terms "isolated polynucleotide" and "polynucleotide in isolated form".

Modification(s): In the context of the present invention the term "modification(s)" is intended to mean any chemical modification of the polypeptide consisting of the amino acid sequence: G-$X_1$-$X_2$-$X_3$-R-$X_4$-$X_5$-$X_6$-K-I-$X_7$-$X_8$-K-$X_9$-$X_{10}$-K-$X_{11}$-$X_{12}$-Z (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}$-$X_{14}$-I-K-$X_{15}$-$X_{16}$-$X_{17}$-$X_{18}$-L-V-P (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or the amino acid sequence shown as amino acids 1 to 29 of anyone of SEQ ID NO:1 to SEQ ID NO:57 or amino acids 1 to 19 of anyone of SEQ ID NO:58 to SEQ ID NO:69 as well as genetic manipulation of the DNA encoding the polypeptides. The modification(s) can be replacement(s) of the amino acid side chain(s), substitution(s), deletion(s) and/or insertions(s) in or at the amino acid(s) of interest; or use of unnatural amino acids with similar characteristics in the amino acid sequence. In particular the modification(s) can be amidations, such as amidation of the C-terminus.

cDNA: The term "cDNA" when used in the present context, is intended to cover a DNA molecule which can be prepared by reverse transcription from a mature, spliced, mRNA molecule derived from a eukaryotic cell. cDNA lacks the intron sequences that are usually present in the corresponding genomic DNA. The initial, primary RNA transcript is a precursor to mRNA and it goes through a series of processing events before appearing as mature spliced mRNA. These events include the removal of intron sequences by a process called splicing. When cDNA is derived from mRNA it therefore lacks intron sequences.

Nucleic acid construct: When used herein, the term "nucleic acid construct" means a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" is defined herein as a configuration in which a control sequence is appropriately placed at a position relative to the coding sequence of the DNA sequence such that the control sequence directs the expression of a polypeptide.

Coding sequence: When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically include DNA, cDNA, and recombinant nucleotide sequences.

Expression: In the present context, the term "expression" includes any step involved in the production of the polypeptide including, but not limited to, transcription, post-transcriptional modification, translation, and post-translational modification. Preferably expression also comprise secretion of the polypeptide.

Expression vector: In the present context, the term "expression vector" covers a DNA molecule, linear or circular, that comprises a segment encoding a polypeptide of the invention, and which is operably linked to additional segments that provide for its transcription.

Host cell: The term "host cell", as used herein, includes any cell type which is susceptible to transformation with a nucleic acid construct.

The terms "polynucleotide probe", "hybridization" as well as the various stringency conditions are defined in the section titled "Polypeptides Having Antimicrobial Activity".

DETAILED DESCRIPTION

Polypeptides Having Antimicrobial Activity

In a first aspect, the present invention relates to polypeptides having antimicrobial activity and where the polypeptides comprises, preferably consists of the amino acid sequence: $G-X_1-X_2-X_3-R-X_4-X_5-X_6-K-I-X_7-X_8-K-X_9-X_{10}-K-X_{11}-X_{12}-Z$ (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}-X_{14}-I-K-X_{15}-X_{16}-X_{17}-X_{18}-L-V-P$ (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or amino acids 1 to 29 of anyone of SEQ ID NO:1 to SEQ ID NO:57 or amino acids 1 to 19 of anyone of SEQ ID NO:58 to SEQ ID NO:69. In an interesting embodiment, the amino acid sequence differs by at the most five amino acids (e.g. by five amino acids), such as by at the most four amino acids (e.g. by four amino acids), e.g. by at the most three amino acids (e.g. by three amino acids), particularly by at the most two amino acids (e.g. by two amino acids), such as by one amino acid from the amino acid sequence: $G-X_1-X_2-X_3-R-X_4-X_5-X_6-K-I-X_7-X_8-K-X_9-X_{10}-K-X_{11}-X_{12}-Z$ (amino acids 1-19 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}-X_{14}-I-K-X_{15}-X_{16}-X_{17}-X_{18}-L-V-P$ (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or amino acids 1 to 29 of anyone of SEQ ID NO:1 to SEQ ID NO:57 or amino acids 1 to 19 of anyone of SEQ ID NO:58 to SEQ ID NO:69.

The term "anyone of SEQ ID NO:1 to SEQ ID NO:57" is intended to mean SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56 or SEQ ID NO:57.

The term "anyone of SEQ ID NO:58 to SEQ ID NO:69" is intended to mean SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68 or SEQ ID NO:69.

Preferably, the polypeptides of the present invention comprise the amino acid sequence of anyone of SEQ ID NO:1 to SEQ ID NO:57 or the amino acid sequence of anyone of SEQ ID NO:58 to SEQ ID NO:69; or a fragment thereof that has antimicrobial activity. In another preferred embodiment, the polypeptide of the present invention comprises amino acids 1 to 29 of anyone of SEQ ID NO: 1 to SEQ ID NO:57 or amino acids 1 to 19 of anyone of SEQ ID NO:58 to SEQ ID NO:69. In a further preferred embodiment, the polypeptide consists of amino acids 1 to 29 of anyone of SEQ ID NO:1 to SEQ ID NO:57 or amino acids 1 to 19 of anyone of SEQ ID NO:58 to SEQ ID NO:69.

The amino acids making up the polypeptides of the invention may independently be selected from D or L forms.

The polypeptide of the invention may be an artificial variant which comprises, preferably consists of, an amino acid sequence that has at the most three, e.g. at the most two, such as at the most one, substitutions, deletions and/or insertions of amino acids as compared to the amino acid sequence: $G-X_1-$ $X_2$-$X_3$-R-$X_4$-$X_5$-$X_6$-K-I-$X_7$-$X_8$-K-$X_9$-$X_{10}$-K-$X_{11}$-$X_{12}$-Z (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}$-$X_{14}$-I-K-$X_{15}$-$X_{16}$-$X_{17}$-$X_{18}$-L-V-P (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or amino acids 1 to 29 of anyone of SEQ ID NO:1 to SEQ ID NO:57 or amino acids 1 to 19 of anyone of SEQ ID NO:58 to SEQ ID NO:69. Such artificial variants may be constructed by standard techniques known in the art, such as by site-directed/random mutagenesis of the polypeptide comprising the amino acid sequence shown as the amino acid sequence: G-$X_1$-$X_2$-$X_3$-R-$X_4$-$X_5$-$X_6$-K-I-$X_7$-$X_8$-K-$X_9$-$X_{10}$-K-$X_{11}$-$X_{12}$-Z (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}$-$X_{14}$-I-K-$X_{15}$-$X_{16}$-$X_{17}$-$X_{18}$-L-V-P (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or amino acids 1 to 29 of anyone of SEQ ID NO:1 to SEQ ID NO:57 or amino acids 1 to 19 of anyone of SEQ ID NO:58 to SEQ ID NO:69. In one embodiment of the invention, amino acid changes are of a minor nature, that is conservative amino acid substitutions that do not significantly affect the folding and/or activity of the protein; small deletions, typically of one to about 5 amino acids; small amino-or carboxyl-terminal extensions, such as an amino-terminal methionine residue; a small linker peptide of up to about 10-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In an interesting embodiment of the invention, the amino acid changes are of such a nature that the physico-chemical properties of the polypeptides are altered. For example, amino acid changes may be performed, which improve the thermal stability of the polypeptide, which alter the substrate specificity, which changes the pH optimum, and the like.

N-Terminal Extension

An N-terminal extension of the polypeptides of the Invention may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE and DD.

Kex2 Sites

Kex2 sites (see, e.g., Methods in Enzymology Vol 185, ed. D. Goeddel, Academic Press Inc. (1990), San Diego, Calif., "Gene Expression Technology") and kex2-like sites are di-basic recognition sites (i.e., cleavage sites) found between the pro-peptide encoding region and the mature region of some proteins.

Insertion of a kex2 site or a kex2-like site have in certain cases been shown to improve correct endopeptidase processing at the pro-peptide cleavage site resulting in increased protein secretion levels.

In the context of the invention insertion of a kex2 or kex2-like site result in the possibility to obtain cleavage at a certain position in the N-terminal extension resulting in an antimicrobial polypeptide being extended in comparison to the mature polypeptide shown as the amino acid sequence: G-$X_1$-$X_2$-$X_3$-R-$X_4$-$X_5$-$X_6$-K-I-$X_7$-$X_8$-K-$X_9$-$X_{10}$-K-$X_{11}$-$X_{12}$-Z (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}$-$X_{14}$-I-K-$X_{15}$-$X_{16}$-$X_{17}$-$X_{18}$-L-V-P (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or amino acids 1 to 29 of anyone of SEQ ID NO:1 to SEQ ID NO:57 or amino acids 1 to 19 of anyone of SEQ ID NO:58 to SEQ ID NO:69.

Fused Polypeptides

The polypeptides of the present invention also include fused polypeptides or cleavable fusion polypeptides in which another polypeptide is fused at the N-terminus or the C-terminus of the polypeptide of the invention or a fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides and Nucleotide Sequences

The present invention also relates to polynucleotides having a nucleotide sequence which encodes for a polypeptide of the invention. In particular, the present invention relates to polynucleotides consisting of a nucleotide sequence which encodes for a polypeptide of the invention. Due to the degeneracy of the genetic code, the skilled person will easily recognize that several nucleotide sequences encoding each of the polypeptides of the invention may be prepared. It is well known in the art which nucleotides make up codons encoding the amino acids of the polypeptides of the invention.

The present invention also relates to polynucleotides which encode fragments of the amino acid sequence: G-$X_1$-$X_2$-$X_3$-R-$X_4$-$X_5$-$X_6$-K-I-$X_7$-$X_8$-K-$X_9$-$X_{10}$-K-$X_{11}$-$X_{12}$-Z (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}$-$X_{14}$-I-K-$X_{15}$-$X_{16}$-$X_{17}$-$X_{18}$-L-V-P (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or anyone of SEQ ID NO:1 to SEQ ID NO:57 or anyone of SEQ ID NO:58 to SEQ ID NO:69 that have antimicrobial activity. A subsequence of the polynucleotides is a nucleotide sequence wherein one or more nucleotides from the 5' and/or 3' end have been deleted.

The nucleotide sequence may be obtained by standard cloning procedures used in genetic engineering to relocate the nucleotide sequence from one location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

Modification of a nucleotide sequence encoding a polypeptide of the present invention may be necessary for the synthesis of a polypeptide, which comprises an amino acid sequence that has at least one substitution, deletion and/or insertion as compared to the amino acid sequence: $G-X_1-X_2-X_3-R-X_4-X_5-X_6-K-I-X_7-X_8-K-X_9-X_{10}-K-X_{11}-X_{12}-Z$ (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}-X_{14}-I-K-X_{15}-X_{16}-X_{17}-X_{18}-L-V-P$ (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or amino acids 1 to 29 of anyone of SEQ ID NO:1 to SEQ ID NO:57 or amino acids 1 to 19 of anyone of SEQ ID NO:58 to SEQ ID NO:69. These artificial variants may differ in some engineered way from the polypeptide isolated from its native source, e.g., variants that differ in specific activity, thermostability, pH optimum, or the like.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for antimicrobial activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding a polypeptide of the present invention may be modified by Introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, *Protein Expression and Purification* 2: 95-107.

Nucleic Acid Constructs

The present invention also relates to nucleic acid constructs comprising a nucleotide sequence of the present invention operably linked to one or more control sequences that direct the expression of the coding sequence in a suitable host cell under conditions compatible with the control sequences.

A nucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* or agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for

*Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising the nucleic acid construct of the invention. The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus,*

*Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, Insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a *Candida*, *Hansenula*, *Kluyveromyces*, *Pichia*, *Saccharomyces*, *Schizosaccharomyces*, or *Yarrowia* cell.

In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma*.

In a most preferred embodiment, the filamentous fungal host cell is an *Aspergillus awamori*, *Aspergillus foetidus*, *Aspergillus japonicus*, *Aspergillus nidulans*, *Aspergillus niger* or *Aspergillus oryzae* cell. In another most preferred embodiment, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens*, *Humicola lanuginosa*, *Mucor miehei*, *Myceliophthora thermophila*, *Neurospora crassa*, *Penicillium purpurogenum*, *Thielavia terrestris*, *Trichoderma harzianum*, *Tichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and Inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having antimicrobial activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor. The recovered polypeptide, plant or plant part may also be used to improve or alter digestive flora in animals and livestock.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, potato, sugar beet, legumes, such as lupins, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleotide sequence encoding a polypeptide of the present invention operably linked with appropriate regulatory sequences required for expression of the nucleotide sequence in the plant or plant part of choice. Furthermore, the expression construct may comprise a selectable marker useful for Identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is Incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleotide sequence encoding a polypeptide having antimicrobial activity of the present invention under conditions conducive for production of the polypeptide; and (b) recovering the polypeptide.

Compositions

In a still further aspect, the present invention relates to compositions, such as pharmaceutical compositions, comprising an antimicrobial polypeptide of the invention.

The composition may comprise a polypeptide of the invention as the major polypeptide component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may further comprise another pharmaceutically active agent, such as an additional biocidal agent, such as another antimicrobial polypeptide exhibiting antimicrobial activity as defined above. The biocidal agent may be an antibiotic, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. The biocidal agent may also be an anti-mycotic agent, including polyenes, e.g. amphotericin B, nystatin; 5-flucosyn; and azoles, e.g. miconazol, ketoconazol, itraconazol and fluconazol.

In an embodiment the biocidal agent is a non-enzymatic chemical agent. In another embodiment the biocidal agent is a non-polypeptide chemical agent.

The biocidal agent may be capable of reducing the number of living cells of *Escherichia coli* (DSM 1576) to $1/100$ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the biocidal agent.

The biocidal agent may also be capable of inhibiting the outgrowth of *Escherichia coli* (DSM 1576) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The biocidal agent may also be capable of reducing the number of living cells of *Bacillus subtilis* (ATCC 6633) to $1/100$ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the biocidal agent.

The biocidal agent may also be capable of inhibiting the outgrowth of *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The compositions may comprise a suitable carrier material. The compositions may also comprise a suitable delivery vehicle capable of delivering the antimicrobial polypeptides of the invention to the desired locus when the compositions are used as a medicament.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Methods and Uses

The present invention also encompasses various uses of the antimicrobial polypeptides of the invention. The antimicrobial polypeptides are typically useful at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, the present invention may also be used in all applications for which known antimicrobial compositions are useful, such as protection of wood, latex, adhesive, glue, paper, cardboard, textile, leather, plastics, caulking, and feed.

Other uses include preservation of foods, beverages, cosmetics such as lotions, creams, gels, ointments, soaps, shampoos, conditioners, antiperspirants, deodorants, mouth wash, contact lens products, enzyme formulations, or food ingredients.

Thus, the antimicrobial polypeptides of the invention may by useful as a disinfectant, e.g., in the treatment of acne, infections in the eye or the mouth, skin infections; in antiperspirants or deodorants; in foot bath salts; for cleaning and disinfection of contact lenses, hard surfaces, teeth (oral care), wounds, bruises and the like.

In general it is contemplated that the antimicrobial polypeptides of the present invention are useful for cleaning, disinfecting or inhibiting microbial growth on any hard surface. Examples of surfaces, which may advantageously be contacted with the antimicrobial polypeptides of the invention are surfaces of process equipment used e.g. dairies, chemical or pharmaceutical process plants, water sanitation systems, oil processing plants, paper pulp processing plants, water treatment plants, and cooling towers. The antimicrobial polypeptides of the invention should be used in an amount, which is effective for cleaning, disinfecting or inhibiting microbial growth on the surface in question.

Further, it is contemplated that the antimicrobial polypeptides of the invention can advantageously be used in a cleaning-in-place (C.I.P.) system for cleaning of process equipment of any kind.

The antimicrobial polypeptides of the Invention may additionally be used for cleaning surfaces and cooking utensils in food processing plants and in any area in which food is prepared or served such as hospitals, nursing homes, restaurants, especially fast food restaurants, delicatessens and the like. It may also be used as an antimicrobial in food products and would be especially useful as a surface antimicrobial in cheeses, fruits and vegetables and food on salad bars.

It may also be used as a preservation agent or a disinfection agent in water based paints.

The antimicrobial polypeptides of the present invention are also useful for microbial control of water lines, and for disinfection of water, in particular for disinfection of industrial water.

The invention also relates to the use of an antimicrobial polypeptide or composition of the invention as a medicament. Further, an antimicrobial polypeptide or composition of the invention may also be used for the manufacture of a medicament for controlling or combating microorganisms, such as fungal organisms or bacteria, preferably gram positive bacteria.

The composition and antimicrobial polypeptide of the invention may be used as an antimicrobial veterinarian or human therapeutic or prophylactic agent. Thus, the composition and antimicrobial polypeptide of the invention may be used in the preparation of veterinarian or human therapeutic agents or prophylactic agents for the treatment of microbial infections, such as bacterial or fungal infections, preferably gram positive bacterial infections. In particular the microbial infections may be associated with lung diseases including, but not limited to, tuberculosis, pneumonia and cystic fibrosis; and sexual transmitted diseases including, but not limited to, gonorrhea and chlamydia.

The composition of the invention comprises an effective amount of the antimicrobial polypeptide of the invention.

The term "effective amount" when used herein is intended to mean an amount of the antimicrobial polypeptide comprising the amino acid sequence: G-$X_1$-$X_2$-$X_3$-R-$X_4$-$X_5$-$X_6$-K-I-$X_7$-$X_8$-K-$X_9$-$X_{10}$-K-$X_{11}$-$X_{12}$-Z (amino acids 1-19 or 1-29 of SEQ ID NO: 1); wherein $X_1$=L or R; $X_2$=L, V, I or F; $X_3$=R or K; $X_4$=L, V, I or F; $X_5$=R, K, W or G; $X_6$=K, R, G, M, N or E; $X_7$=G, R, K or E; $X_8$=G, R, K or E; $X_9$=L or F; $X_{10}$=K or R; $X_{11}$=I, L, F, C or Y; $X_{12}$=G, A or T; Z=R or $X_{13}$-$X_{14}$-I-K-$X_{15}$-$X_{16}$-$X_{17}$-$X_{18}$-L-V-P (amino acids 19-29 of SEQ ID NO: 1); wherein $X_{13}$=Q, L or P; $X_{14}$=K, I, M, L or V; $X_{15}$=P, A, H, N or D; $X_{16}$=I or L; $X_{17}$=R, H, Q or P; $X_{18}$=I or K; or the amino acid sequence shown as amino acids 1 to 29 of anyone of SEQ ID NO:1 to SEQ ID NO:57 or amino acids 1 to 19 of anyone of SEQ ID NO:58 to SEQ ID NO:69, or a fragment or a variant thereof, which is sufficient to inhibit growth of the microorganisms in question.

The invention also relates to wound healing compositions or products such as bandages, medical devices such as, e.g., catheters and further to anti-dandruff hair products, such as shampoos.

Formulations of the antimicrobial polypeptides of the invention are administered to a host suffering from or predisposed to a microbial infection. Administration may be topical, localized or systemic, depending on the specific microorganism, preferably it will be localized. Generally the dose of the antimicrobial polypeptides of the invention will be sufficient to decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use. The antimicrobial polypeptides of the invention are particularly useful for killing gram negative bacteria, including *Pseudomonas aeruginosa*, and *Chlamydia trachomatis*; and gram-positive bacteria, including various staphylococci and streptococci.

The antimicrobial polypeptides of the invention are also useful for in vitro formulations to kill microbes, particularly where one does not wish to introduce quantities of conventional antibiotics. For example, the antimicrobial polypeptides of the invention may be added to animal and/or human food preparations; or they may be included as an additive for in vitro cultures of cells, to prevent the overgrowth of microbes in tissue culture.

The susceptibility of a particular microbe to killing with the antimicrobial polypeptides of the invention may be determined by in vitro testing, as detailed in the experimental section. Typically a culture of the microbe is combined with the antimicrobial polypeptide at varying concentrations for a period of time sufficient to allow the protein to act, usually between about one hour and one day. The viable microbes are then counted, and the level of killing determined.

Microbes of interest include, but are not limited to, Gram-negative bacteria, for example: *Citrobacter* sp.; *Enterobacter* sp.; *Escherichia* sp., e.g. *E. coli; Klebsiella* sp.; *Morganella* sp.; *Proteus* sp.; *Providencia* sp.; *Salmonella* sp., e.g. *S. typhi, S. typhimurium; Serratia* sp.; *Shigella* sp.; *Pseudomonas* sp., e.g. *P. aeruginosa; Yersinia* sp., e.g. *Y. pestis, Y. pseudotuberculosis, Y. enterocolitica; Franciscella* sp.; *Pasturella* sp.; *Vibrio* sp., e.g. *V. cholerae, V. parahemolyticus; Campylobacter* sp., e.g. *C. jejune; Haemophilus* sp., e.g. *H. influenzae, H. ducreyi; Bordetella* sp., e.g. *B. pertussis, B. bronchiseptica, B. parapertussis; Brucella* sp., *Neisseria* sp., e.g. *N. gonorrhoeae, N. meningitidis*, etc. Other bacteria of interest include *Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Treponema* sp., e.g. *T. pallidum; Borrelia* sp., e.g. *B. burgdorferi; Leptospirae* sp.; *Rickettsia* sp., e.g. *R. rickettsii, R. typhi; Chiamydia* sp., e.g. *C. trachomatis, C. pneumoniae, C. psittaci; Helicobacter* sp., e.g. *H. pylori*, etc.

Non bacterial pathogens of interest include fungal and protozoan pathogens, e.g. *Plasmodia* sp., e.g. *P. falciparum, Trypanosoma* sp., e.g. *T. brucei*; shistosomes; *Entaemoeba* sp., *Cryptococcus* sp., *Candida* sp., e.g. *C. albicans*; etc.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific antimicrobial polypeptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The antimicrobial polypeptides of the invention may be systemic after administration or may be localized by the use of an implant or other formulation that acts to retain the active dose at the site of implantation.

In one embodiment, a formulation for topical use comprises a chelating agent that decreases the effective concentration of divalent cations, particularly calcium and magnesium. For example, agents such as citrate, EGTA or EDTA may be included, where citrate is preferred. The concentration of citrate will usually be from about 1 to 10 mM.

The compounds of the present invention can be administered alone, in combination with each other, or they can be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 pg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al. (1991) *J. Biol. Chem.* 266:3361 may be used. Briefly, the lipids and lumen composition containing peptides are combined in an appropriate aqueous medium, conveniently a saline medium where the total solids will be in the range of about 1-10 weight percent. After intense agitation for short periods of time, from about 5-60 sec., the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Formulations with Other Active Agents

For use in the subject methods, the antimicrobial polypeptides of the invention may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a formulation of the antimicrobial polypeptides of the invention, e.g. interferon gamma, tumor necrosis factor alpha, interleukin 12, etc.

In Vitro Synthesis

The antimicrobial peptides of the invention may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein Animal Feed The present invention is also directed to methods for using the polypeptides having antimicrobial activity in animal feed, as well as to feed compositions and feed additives comprising the antimicrobial polypeptides of the invention.

The term animal includes all animals, including human beings. Examples of animals are non-ruminants, and ruminants, such as cows, sheep and horses. In a particular embodiment, the animal is a non-ruminant animal. Non-ruminant animals include mono-gastric animals, e.g. pigs or swine (including, but not limited to, piglets, growing pigs, and sows); poultry such as turkeys and chicken (including but not limited to broiler chicks, layers); young calves; and fish (including but not limited to salmon).

The term feed or feed composition means any compound, preparation, mixture, or composition suitable for, or intended for intake by an animal.

In the use according to the invention the antimicrobial polypeptide can be fed to the animal before, after, or simultaneously with the diet. The latter is preferred.

In a particular embodiment, the antimicrobial polypeptide, in the form in which it is added to the feed, or when being included in a feed additive, is well defined. Well-defined means that the antimicrobial polypeptide preparation is at least 50% pure as determined by Size-exclusion chromatography (see Example 12 of WO 01/58275). In other particular embodiments the antimicrobial polypeptide preparation is at least 60, 70, 80, 85, 88, 90, 92, 94, or at least 95% pure as determined by this method.

A well-defined antimicrobial polypeptide preparation is advantageous. For instance, it is much easier to dose correctly to the feed an antimicrobial polypeptide that is essentially free from interfering or contaminating other antimicrobial polypeptides. The term dose correctly refers in particular to the objective of obtaining consistent and constant results, and the capability of optimising dosage based upon the desired effect.

For the use in animal feed, however, the antimicrobial polypeptide need not be that pure; it may e.g. include other enzymes, in which case it could be termed an antimicrobial polypeptide preparation.

The antimicrobial polypeptide preparation can be (a) added directly to the feed (or used directly in a treatment process of vegetable proteins), or (b) it can be used in the production of one or more intermediate compositions such as feed additives or premixes that is subsequently added to the feed (or used in a treatment process). The degree of purity described above refers to the purity of the original antimicrobial polypeptide preparation, whether used according to (a) or (b) above.

Antimicrobial polypeptide preparations with purities of this order of magnitude are in particular obtainable using recombinant methods of production, whereas they are not so easily obtained and also subject to a much higher batch-to-batch variation when the antimicrobial polypeptide is produced by traditional fermentation methods.

Such antimicrobial polypeptide preparation may of course be mixed with other enzymes.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

The antimicrobial polypeptide can be added to the feed in any form, be it as a relatively pure antimicrobial polypeptide, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the antimicrobial polypeptide of the invention, the animal feed additives of the invention contain at least one fat soluble vitamin, and/or at least one water soluble vitamin, and/or at least one trace mineral, and/or at least one macro mineral.

Further, optional, feed-additive ingredients are colouring agents, aroma compounds, stabilisers, and/or at least one other enzyme selected from amongst phytases EC 3.1.3.8 or 3.1.3.26; xylanases EC 3.2.1.8; galactanases EC 3.2.1.89; and/or beta-glucanases EC 3.2.1.4.

In a particular embodiment these other enzymes are well defined (as defined above for antimicrobial polypeptide preparations).

Examples of other antimicrobial peptides (AMP's) are CAP18, Leucocin A, Tritrpticin, Protegrin-1, Thanatin, Defensin, Ovispirin such as Novispirin (Robert Lehrer, 2000), and variants, or fragments thereof which retain antimicrobial activity.

Examples of other antifungal polypeptides (AFP's) are the *Aspergillus giganteus*, and *Aspergillus niger* peptides, as well as variants and fragments thereof which retain antifungal activity, as disclosed in WO 94/01459 and PCT/DK02/00289 [replace with WO number once published].

Usually fat and water soluble vitamins, as well as trace minerals form part of a so-called premix intended for addition to the feed, whereas macro minerals are usually separately added to the feed. Either of these composition types, when enriched with an antimicrobial polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat soluble vitamins are vitamin A, vitamin D3, vitamin E, and vitamin K, e.g. vitamin K3.

Examples of water soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, Iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one antimicrobial polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the Invention contains 0-80% maize; and/or 0-80% sorghum; and/or 0-70% wheat; and/or 0-70% Barley; and/or 0-30% oats; and/or 040% soybean meal; and/or 0-10% fish meal; and/or 0-20% whey. Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 5-30 mg enzyme protein per kg animal diet.

The antimicrobial polypeptide may be administered in one or more of the following amounts (dosage ranges): 0.01-200; or 0.01-100; or 0.05-100; or 0.05-50; or 0.10-10—all these ranges being in mg antimicrobial polypeptide protein per kg feed (ppm).

For determining mg antimicrobial polypeptide protein per kg feed, the antimicrobial polypeptide is purified from the feed composition, and the specific activity of the purified antimicrobial polypeptide is determined using a relevant assay (see under antimicrobial activity, substrates, and assays). The antimicrobial activity of the feed composition as such is also determined using the same assay, and on the basis of these two determinations, the dosage in mg antimicrobial polypeptide protein per kg feed is calculated.

The same principles apply for determining mg antimicrobial polypeptide protein in feed additives. Of course, if a sample is available of the antimicrobial polypeptide used for preparing the feed additive or the feed, the specific activity is determined from this sample (no need to purify the antimicrobial polypeptide from the feed composition or the additive).

Detergent Composition

The antimicrobial polypeptides of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the Invention provides a detergent additive comprising the antimicrobial polypeptides of the invention and a surfactant. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase (such as a laccase), and/or a peroxidase (such as a haloperoxidase).

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzen* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothemmophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Cellulases: Suitable cellulases Include those of bacterial or fungal origin. Chemically modified or protein engineered mutants are included. Suitable cellulases include cellulases from the genera *Bacillus*, *Pseudomonas*, *Humicola*, *Fusarum*, *Thielavia*, *Acremonium*, e.g. the fungal cellulases produced from *Humicola insolens*, *Myceliophthora thermo-* phila and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, and the antimicrobial polypeptides of the invention, may be added in an amount corresponding to 0.01-100 mg of enzyme protein per liter of wash liqour, preferably 0.05-10 mg of enzyme protein per liter of wash liqour, more preferably 0.1-5 mg of enzyme protein per liter of wash liqour, and most preferably 0.1-1 mg of enzyme protein per liter of wash liqour.

The antimicrobial polypeptides of the invention may additionally be incorporated in the detergent formulations disclosed in WO 97/07202 which is hereby incorporated as reference.

The present invention is further described by the following examples which should not be construed as limiting the scope of the invention.

EXAMPLES

Chemicals used as buffers and substrates were commercial products of at least reagent grade.

Example 1

Cloning, Expression and Activity Evaluation of an Antimicrobial Polypeptide (Cat1)

Cloning of Synthetic Gene Encoding Cat1

In order to produce the antimicrobial polypeptide Cat1 (SEQ ID NO:3) for antimicrobial activity assays, a synthetic gene was made (see below) and inserted into the expression vector pET31b+ (Novagen Inc.). The synthetic gene was constituted by specifically designed oligonucleotides (Primer1 and Primer2).

Synthetic gene encoding Cat1 (SEQ ID NO: 70):
```
GGC CTG CTG CGC CGT CTG CGC AAG AAG ATT GGC AAA
 G   L   L   R   R   L   R   K   K   I   G   K AAG CTG AAG AAA ATT GGC CAG AAG ATT AAA CCG ATT
 K   L   K   K   I   G   Q   K   I   K   P   I

CGC ATT CTG GTG CCG TAG
 R   I   L   V   P   *
```

Primer1 (SEQ ID NO: 72):
ATTATTCAGA TGCTGGATCC GGCGGAAGGC CTGCTGCGCC

GTCTGCGCAA GAAGATTGGC AAAAAGCTGA AGAAAATTGG

CCAGAAGATT AAACCGATTC GCATTCTGGT GCCGTAGCTC

GAGATTATT

Primer2 (SEQ ID NO: 73):
AATAATCTCG AGCTACGGCA CCAGAATGCG AATCGGTTTA

ATCTTCTGGC CAATTTTCTT CAGCTTTTTG CCAATCTTCT

TGCGCAGACG GCGCAGCAGG CCTTCCGCCG GATCCAGCAT

CTGAATAAT

Enzymatic digestion of flanking restriction endonuclease sites (AlwNI/AvaI) enabled us to clone this synthetic gene as a fusion construct in pET31b+ (standard procedures as described by the manufacturer, New England Biolabs Inc.). All standard protocols have been described elsewhere (Sambrook, Fritsch, and Maniatis, 1989).

Transformation and Expression of Cat1 in *E. coli*

Recombinant pET31 b+ was transformed into *E. coli* Novablue as described by the manufacturer (Novagen). Plasmid was prepared by QIAprep Mini Columns (QIAGEN Inc.) and sequenced by automated sequencing using plasmid specific primers (Primer3 and Primer4):

Primer3 (SEQ ID NO:74):
TGCTA GTTAT TGCTC AGCGG

Primer4 (SEQ ID NO: 75):
ACCGT AGTTG CGCCC ATCG

Plasmid was transformed in *E. Coli* BLR-DE3 according to the manufacturer (Novagen). Bacteria were cultivated in LB media to $OD_{600}$~0.8 and recombinant protein synthesis was initiated by 1 mM IPTG (Isopropyl beta-D-Thiogalactopyranoside). Upon 3 hours of induction, bacteria were harvested, re-suspended in 1/10 volume buffer A (50 mM Tris-HCl, 1 mM EDTA, 100 mM NaCl, pH 8) and lysed by pressure disruption (1500 mBar). Resulting pellet was washed twice in buffer B (50 mM Tris-HCl, 10 mM EDTA, 0.5% TritonX-100, 100 mM NaCl, pH 8). All standard protocols have been described elsewhere (Sambrook, Fritsch, and Maniatis, 1989).

Purification of Cat1 from *E. coli* Inclusion Bodies

The pellet resulting from the above purification contained purified inclusion bodies. To liberate the peptide from the KSI fusion partner, acid hydrolysis was performed on an engineered Asp-Pro site, introduced N-terminally to the gene encoding Cat1. Inclusion bodies were re-suspended in 100 mM sodium phosphate (pH 2.3) and incubated overnight at 85 degrees Celsius. Resulting supernatant contained peptide (PAE-Cat1). The sample was neutralized by adding 100 mM sodium phosphate (pH 12.3). In order to maturate the peptide, the peptide was treated with a glutamyl endopeptidase I (from *B. licheniformis*). The maturated peptide was confirmed by mass-spectrometry and further purified by standard chromatographic procedures.

Antimicrobial Activity by NCCLS Microdilution Broth Assay (MIC & MBC)

According to the NCCLS guidelines for susceptibility test of novel antimicrobial compounds, we found a broad spectrum of activity of Cat1 (Methods for Dilution Antimicrobial Susceptibility Tests for Bacteria That Grow Aerobically; Approved Standard-Fifth Edition. NCCLS document M7-A5 (ISBN1-56238-394-9)). The following bacteria strains were susceptible to Cat1 (MIC<64 µg/ml): *Bacillus subtilis* (ATCC6633), *Micrococcus luteus* (ATCC9341), *Staphylococcus epidermidis* (DSM1798), *Enterococcus faecalis* (DSM2570), *Pseudomonas aeruginosa* (ATCC27853), *Bortadella bronchiseptica* (ATCC4617), *Eschericia coil* (ATCC10536), *Klepsiella pneumoniae* (ATCC10031), *Salmonella choleraesuis* (DSM9220) and *Proteus mirabilis* (ATCC7002). Minimal bactericidal concentration (MBC) was in a similar range, indicating that the activity of Cat1 is bactericidal.

In another campaign, the specific MICs of Cat1 were determined against a variety of microbial strains relevant for wound infections. As recommended in the above-mentioned NCCLS protocol, the strains were grown in cationic adjusted Muller-Hinton Broth. The highest concentration tested was 32 µg/ml. The results in Table I show that Cat1 is a broad-spectrum antibiotic with potent activities against a range of different Gram-negative and Gram-positive bacteria.

TABLE 1

| Microbial strain | ATCC# | MIC (µg/ml) |
| --- | --- | --- |
| *Pseudomonas aeruginosa* | 27853 | 2 |
| *Staphylococcus aureus* (MSSA) | 25923 | 32 |
| *Staphyloloccus aureus* GISA | 700699 | 32 |
| *Staphylococcus epidermidis* | 12228 | 4 |
| *Streptococcus pneumoniae* | 10015 | 8 |
| *Stenotrophomonas maltophilia* | 12714 | 1 |
| *Escherichia coli* | 25922 | 1.5 |
| *Streptotoccus pyogenes* | 4543 | 1.5 |
| *Bordetella bronchiseptica* | 14064 | 0.5 |
| *Klebsiella pneumoniae* | 29995 | 8 |
| *Acinetobacter baumanii* | 49137 | 8 |
| *Citrobacter freundii* | 11811 | 1.5 |
| *Morganella morganii* | 21116 | 1.5 |
| *Micrococcus luteus* | 9341 | 0.5 |
| *Streptococcus agalactiae* | 624 | 16 |
| *Aerococcus viridans* | 700406 | 0.5 |
| *Clostridium difficile* | 43594 | 32 |

MIC Values Under Different Test Conditions

Minimal inhibitory concentrations of Cat1 were also determined using cation-adjusted Mueller hinton broth (MHB) in the microbroth dilution assay, wherein MHB was used with different modifications as depicted in Table 2 below. The selected test organism was *Pseudomonas aeruginosa* (ATCC 27853).

TABLE 2

| Test conditions | MIC (µg/ml) |
| --- | --- |
| MHB | 4 |
| MHB + 1.5 mM $Ca^{2+}$ | 11 |
| MHB + 1.5 mM $Mg^{2+}$ | 6 |
| MHB + 150 mM NaCl | 6 |
| MHB + 1% Human Serum | 6 |

TABLE 2-continued

| Test conditions | MIC (µg/ml) |
|---|---|
| MHB + 1% lysed human red blood cells | 9 |
| MHB adjusted to pH 6.5 | 6 |
| MHB adjusted to pH 5.5 | 6 |

Killing Kinetics

The rate of killing of Cat1 was determined in MHB using *Pseudomonas aeroginosa* (ATCC 27853) as the test organism. The bacteria were incubated with Cat1 (at 4×MIC concentration). At different time-points, several dilutions of the preparation were plated and an estimate of viable cells was determined (CFU/ml). The results in Table 3 indicate that Cat1 rapidly kills the bacteria, with a near 3-log reduction in CFU within 30 minutes.

TABLE 3

| | CFU/ml | |
|---|---|---|
| Time | Control | Cat1 |
| 0 hours | 100.000 | 100.000 |
| 0.5 hours | 100.000 | 175 |
| 1.5 hours | 300.000 | <20 |
| 24 hours | >1.000.000 | <20 |

Antimicrobial Activity by Radial Diffusion Assay (MEC)

A modified version of a previously published protocol has been applied in the detection of antimicrobial activity (Lehrer et al., (1991) Ultra sensitive assays for endogenous antimicrobial polypeptides *J Immunol Methods* 137: 167-173). Target bacteria ($10^6$ colony forming units (CFU)) were added to 10 ml of underlay agarose (1% low electro-endosmosis agarose, 0.03% Trypticase soy broth, 10 mM sodium phosphate, pH 7.4, 37 degrees Celsius). Suspension was solidified on an INTEGRID Petri Dish (Becton Dickinson Labware). A 3 mm Gel Puncher was used to make holes in the underlay agarose (Amersham Pharmacia Biotech, Sweden). Samples were added to the holes and incubated at 37 degrees Celsius, 3 hours. An overlay was poured on top and the plate was incubated overnight (LB media, 7.5% Agar). Antimicrobial activity was seen as bacterial clearing zones around the wells. Living cells was counterstained by adding 10 ml, 0.2 mM MTT (3-(4,5-Dimethylthiazol-2-yl)-2,5-diphenyltetrazolium bromide Thiazolyl blue).

This assay revealed similar activity spectrum and concentrations as determined by the NCCLS protocol (above paragraph). The following bacteria species were found to be susceptible (Minimal Effective Concentration (MEC)<64 µg/ml): *Bacillus subtilis* (ATCC6633), *Enterococcus hirae* (ATCC10541), *Micrococcus luteus* (ATCC9341), *Staphylococcus aureus* (ATCC29737), *Staphylococcus epidermidis* (DSM1798), *Enterococcus faecalis* (DSM2570), *Pseudomonas aeroginosa* (ATCC27853), *Bortadella bronchiseptica* (ATCC4617), *Eschericia coli* (ATCC10536), *Klepsiella pneumoniae* (ATCC10031), *Salmonella choleraesuis* (DSM9220) and *Proteus mirabilis* (ATCC7002).

Example 2

Evaluation of Antimicrobial Activity

A range of synthetic antimicrobial polypeptides were expressed in *E. coli* TOP10 (Invitrogen) using arabinose as inducer, as disclosed in Example 1 of International patent application WO 00/73433 (with minor modifications). Expression of the antimicrobial polypeptides of the invention resulted in growth inhibition of the host cells.

Briefly, fresh overnight cultures grown in RM medium containing 0.2% glucose and ampicillin (100 µg/ml) were diluted 300-fold into 150 microliter of RM containing 0.2% glycerol and ampicillin (100 µg/ml) and different concentrations of arabinose (0, 0.01% or 0.1%) in a microtiter plate and incubated at 37 degrees Celsius with vigorous shaking. The growth curve was monitored by measuring OD450 using a Bioscreen C Microbiology reader (Thermo Electron Corporation) at intervals of 30 minutes for 14 hours (see Invitrogen protocol of the pBAD/gIII A, B and C vectors catalogue nos. V450-01 for buffer and media composition).

The percentage of growth inhibition was calculated as the end point OD measurement of each sample divided by the end point OD measurement obtained from cells containing the control vector and multiplied by 100. The formula is the following:

$$\left(1 - \frac{\text{sample } OD - \text{blank } OD}{\text{control vector } OD - \text{blank } OD}\right) \times 100$$

where "blank OD" corresponds to the OD of an empty well.

The amino acid sequences of Cat1 and selected improved synthetic variants are listed in Tables 4, 5 and 6.

TABLE 4

| Amino acid sequence | SEQ ID NO: | Growth inhibition using 0.01% arabinose (%) | Growth inhibition using 0.1% arabinose (%) |
|---|---|---|---|
| GLLRRLRKKIGKKLKKIGQKIKPIRILVP | 3 | 63 | 64 |
| GLLRRLRGKIGKKLKKIGQKIKAIRKLVP | 4 | 89 | 100 |
| GLLRRFRKKIGGKLKKYGQIIKHLRILVP | 5 | 94 | 100 |
| GLLRRLRRKIGGKLKKFGQKIKPLRKLVP | 6 | 92 | 100 |
| GLLRRLRKKIGKKLKFFGQKIKHIRILVP | 7 | 93 | 100 |
| GLLKRLGRKIGKKLKKFGQKIKAIRKLVP | 8 | 97 | 100 |
| GRFKRFWKKIGRKFKKIGQMLKPIRILVP | 9 | 96 | 100 |

TABLE 4-continued

| Amino acid sequence | SEQ ID NO: | Growth inhibition using 0.01% arabinose (%) | Growth inhibition using 0.1% arabinose (%) |
|---|---|---|---|
| GLLKRLRKKIGKKLKKIGPKIKHIRKLVP | 10 | 93 | 100 |
| GLLRRFWMKIGGKLKKFGQMIKHLRKLVP | 11 | 92 | 99 |
| GRLRRLRRKIGEKLKKFGQVIKALRILVP | 12 | 94 | 99 |
| GLLRRLWRKIGRKLKKYGQKIKALRKLVP | 13 | 96 | 100 |
| GRFRRFRKKIGKKLKKIGLVIKHIRILVP | 14 | 94 | 100 |
| GLLRRLRRKIGKKLKKFGQKIKHIRILVP | 15 | 96 | 100 |
| GLLRRLRNKIRKKLKKFGQKIKAIRILVP | 16 | 96 | 100 |
| GRLRRLWRKIGRKLKKYGQVIKHLRILVP | 17 | 94 | 100 |

TABLE 5

| Amino acid sequence | SEQ ID NO: | Growth inhibition using 0.1% arabinose (%) |
|---|---|---|
| GLLRRLRKKIGKKLKKIGQKIKPIRILVP | 3 | 53 |
| GLFKRLRKKIGKKLKKFGQKIKPLRKLVP | 18 | 94 |
| GLLRRFGRKIGKKFKKFGPKIKILRKLVP | 19 | 91 |
| GLFRRFRRKIGKKLKKFGQKIKPLRKLVP | 20 | 97 |
| GLFRRFRRKIGRKLKKYGLMIKPLRKLVP | 21 | 94 |
| GLLKRFRGKIGKKLKKYGQLIKAIRILVP | 22 | 90 |
| GLFRRLRKKIGKKLKKIGQLIKAIRILVP | 23 | 97 |
| GLLRRFGKKIGKKFKKYGQKIKNLRILVP | 24 | 92 |
| GLLKRLRKKIGKKLKKIGQKIKPIRKLVP | 25 | 94 |
| GLLRRFGRKIGKKFKKFGPKIKHLRKLVP | 26 | 92 |
| GRIRRLRRKIRKKLKKYGQKIKAIRKIVP | 27 | 96 |
| GRFRRFRKKIGGKLKKIGQVIKDIRILVP | 28 | 95 |
| GRFRRFRKKIGKKFKKFGQMIKALRILVP | 29 | 95 |
| GRLRRFRKKIGKKLKKIGQMIKHIRILVP | 30 | 95 |
| GLVRRFRRKIGKKLKKIGQIIKAIRKLVP | 31 | 96 |
| GLLRRLRRKIGKKFKKIGQVIKHLRKLVP | 32 | 97 |
| GLFRRLRGKIGKKLKKIGQKIKAIRILVP | 33 | 91 |
| GLFRRLGKKIGKKIKKFGQVIKHIRILVP | 34 | 92 |
| GLLRRLGKKIGKKFKKFGQVIKALRILVP | 35 | 95 |
| GLFRRLGRKIGKKLKKIGQVIKHIRILVP | 36 | 95 |
| GLLRRLRKKIEKKLKKIGPKIKALRKLVP | 37 | 94 |
| GRIKRVGEKIGKKLKKIGQVIKHLRKLVP | 38 | 96 |
| GLFRRFGKKIGKKLKKIGQVIKALRILVP | 39 | 95 |
| GRLRRFGKKIGKKIKKFGQLIKALRILVP | 40 | 95 |
| GLLRRFWKKIGKKLKKFGKIKPLPKLVP | 41 | 96 |
| GRFRRLGRKIGEKLKKFGQVIKAIRILVP | 42 | 95 |
| GLFRRFGKKIGKKIIKKIGQKIKPIHKLVP | 43 | 76 |
| GLLKRLRKKIGKKLKKIGQMIKHIRILVP | 44 | 93 |
| GLLRRFRBEIGKKLKKYGQKIKHLRKLVP | 45 | 79 |
| GLFRRLRRKIGKKFKKFGQKIKPLRKLVP | 46 | 96 |
| GLFRRFWKKIGRKLKKIGQKIKPLQILVP | 47 | 79 |
| GLLRRLWKKIGRKFKKYGQVIKHIRKLVP | 48 | 97 |
| GLLRRLGRKIGKKLKKIGQKIKAIRILVP | 49 | 96 |
| GLLRRFRNKIGKKLKKIGQKIKPIRKLVP | 50 | 92 |
| GRFKRLRKKIGKKFKKIGQKIKDIRKLIVP | 51 | 97 |
| GLFRRIRRKIGKKFKKFGQVIKPLRKLVP | 52 | 95 |
| GRLRRLGKIUGEKLKKFGQMIKHIRILVP | 53 | 84 |
| GLLRRIIGKKIGKKFKKCGQVIKAIRILVP | 54 | 89 |
| GLLRRFRKKIGEKFKKFGQKIKNIRILVP | 55 | 79 |
| GLLRRLRKKIGKKLKKIGQKIKPIRKLVP | 56 | 94 |
| GLLRRFRKKIGKKLKKYGQKIKHLRILVP | 57 | 95 |

TABLE 6

| Amino acid sequence | SEQ ID NO: | Growth inhibition using 0.01% arabinose (%) | Growth inhibition using 0.1% arabinose (%) |
|---|---|---|---|
| GLLRLRKKIGKKLKKIGQKIKPIRILVP | 3 | 65 | 68 |
| GLLRRLRKKIGKKLKKIAR | 59 | 93 | 100 |
| GLFRRLKRKIGRKFKKIAR | 60 | 85 | 99 |
| GLLKRLGRKIGKKFKKIAR | 61 | 89 | 98 |
| GLLRRFRKKIGKKLKKIAR | 62 | 94 | 98 |
| GLLRRLRKKIGKKLKKITR | 63 | 95 | 99 |
| GLFRRLRKKIGKKLKKIAR | 64 | 92 | 99 |
| GLFRRLKRKIGKKLKKIAR | 65 | 91 | 99 |
| GLLKRLGRKIGKKIKKIAR | 66 | 92 | 100 |
| GLLRRFRKKIGKKLKKITR | 67 | 90 | 100 |
| GLLRRLRKKIGRKFKKIAR | 68 | 91 | 100 |
| GLFRRLRKKIGKKFKKIAR | 69 | 86 | 99 |

The results shown in Tables 4, 5 and 6 indicate convincingly that all the tested antimicrobial polypeptides exhibit strong antimicrobial activity.

Example 3

Antimicrobial Activity Against Bacterial Strains (MIC & MEC)

The antimicrobial activity of the polypeptides of the invention was analyzed using the Microdilution Broth Assay (see Example 1) with Mueller Hinton Broth (MHB) media. Four different bacterial strains were tested in this setup; *Micrococcus luteus* (ATCC 9341), *Pseudomonas aeruginosa* (ATCC 27853), *Escherichia coli* (ATCC 10536) and *Klebsiella pneumoniae* (DSM681). The amino acid sequence of the polypeptides and the Minimal Inhibitory concentrations (MIC, microgram/ml) obtained is presented in Table 7 below.

TABLE 7

| | MIC (µg/ml) | | | |
|---|---|---|---|---|
| Amino acid sequence | Micrococcus luteus (ATCC 9341) | Pseudomonas aeruginosa (ATCC 27853) | Escherichia coli (ATCC 10536) | Klebsiella pneumoniae (DSM681) |
| GLLRLRKKIGKKLKKIGQKIKPIRILVP (SEQ ID NO: 3) | 16 | 4 | 8 | 32-64 |
| GLLRRFWKKIGKKLKKFGQKIKPLPKLVP (SEQ ID NO: 41) | 32 | 16 | 32 | 32 |
| GLLRRLWRKIGRKLKKYGQKIKALRKLVP (SEQ ID NO: 13) | 32 | 32 | 64 | 32 |
| GLLRRLRKKIGKKLKKIAR (SEQ ID NO: 59) | 32 | 8 | 16 | 32 |
| GLLKRLGRKIGKKLKKIAR (SEQ ID NO: 66) | 64 | 64 | 8 | Not tested |
| GLLRRFRKKIGKKLKKIAR (SEQ ID NO: 62) | 64 | 64 | 16 | 32-64 |

The antimicrobial activity of the polypeptides of the invention was also analyzed in a Radial Diffusion Assay (see Example 1) using minimal conditions. Two bacterial strains were tested in this setup; *Staphylococcus camosus* and *Escherichia coli* Top10. The amino acid sequence of the polypeptides and the Minimal Effective Concentration (MEC, microgram/ml) obtained is presented in table 8 below.

TABLE 8

| Amino acid sequence | MEC (µg/ml) | |
|---|---|---|
| | *Staphylococcus camosus* | *Escherichia* Top 10 |
| GLLRRLRKKIGKKLKKIGQKIKPI RILVP (SEQ ID NO: 3) | 2.5 | 8.5 |
| GRIKRVGEKIGKKLKKIGQVIKHL RILVP (SEQ ID NO: 38) | 8 | 8.5 |

TABLE 8-continued

| Amino acid sequence | MEC (µg/ml) | |
|---|---|---|
| | *Staphylococcus camosus* | *Escherichia* Top 10 |
| GLLRRFWKKIGKKLKKFGQKIKPL PKLVP (SEQ ID NO: 41) | 3.8 | 16.6 |
| GLLRRLWRKIGRKLKKYGQKIKAL RKLVP (SEQ ID NO: 13) | 4.4 | 27.0 |
| GLLRRLRKKIGKKLKKIAR (SEQ ID NO: 59) | 1.8 | 18.3 |
| GLLKRLGRKIGKKLKKIAR (SEQ ID NO: 66) | 2 | 13.5 |
| GLLRRFRKKIGKKLKKIAR (SEQ ID NO: 62) | 1.1 | 28.0 +TZ,1/32 |

The invention claimed is:

1. An isolated polypeptide having antimicrobial activity, comprising the amino acid sequence of SEQ ID NO: 1:

```
                                              (SEQ ID NO: 1)
Gly Xaa Xaa Xaa Arg Xaa Xaa Xaa Lys Ile Xaa Xaa
            5                   10

Lys Xaa Xaa Lys Xaa Xaa Xaa Xaa Ile Lys Xaa Xaa
        15                  20

Xaa Xaa Leu Val Pro;
25
``` wherein
Xaa at position 2 is Leu or Arg;
Xaa at position 3 is Leu, Val, Ile or Phe;
Xaa at position 4 is Arg or Lys;
Xaa at position 6 is Leu, Val, Ile or Phe;
Xaa at position 7 is Arg, Lys, Trp or Gly;
Xaa at position 8 is Lys, Arg, Gly, Met, Asn or Glu;
Xaa at position 11 is Gly, Arg, Lys or Glu;
Xaa at position 12 is Gly, Arg, Lys or Glu;
Xaa at position 14 is Leu or Phe;
Xaa at position 15 is Lys or Arg;
Xaa at position 17 is Ile, Leu, Phe, Cys or Tyr;
Xaa at position 18 is Gly, Ala or Thr;
Xaa at position 19 is Gln, Arg, Leu or Pro;
Xaa at position 20 is Lys, Ile, Met, Leu or Val;
Xaa at position 23 is Pro, Ala, His, Asn or Asp;
Xaa at position 24 is Ile or Leu;
Xaa at position 25 is Arg, His, Gln or Pro; and
Xaa at position 26 is Ile or Lys;
wherein each amino acid is independently the D or L form.

2. The polypeptide of claim 1, wherein Xaa at position 3 is Leu or Phe.

3. The polypeptide of claim 1, wherein Xaa at position 6 is Leu or Phe.

4. The polypeptide of claim 1, wherein Xaa at position 7 is Arg, Lys or Gly.

5. The polypeptide of claim 1, wherein Xaa at position 8 is Lys, Arg or Glu.

6. The polypeptide of claim 1, wherein Xaa at position 11 is Gly or Lys.

7. The polypeptide of claim 1, wherein Xaa at position 12 is Lys, Arg or Glu.

8. The polypeptide of claim 1, wherein Xaa at position 17 is Ile or Leu.

9. The polypeptide of claim 1, wherein Xaa at position 18 is Ala or Thr.

10. The polypeptide of claim 1, wherein
Xaa at position 3 is Leu or Phe;
Xaa at position 4 is Arg or Lys;
Xaa at position 6 is Leu or Phe;
Xaa at position 7 is Arg, Lys or Gly;
Xaa at position 8 is Lys, Arg or Glu;
Xaa at position 11 is Gly or Lys;
Xaa at position 12 is Lys, Arg or Glu;
Xaa at position 17 is Ile or Leu; and
Xaa at position 18 is Ala or Thr.

11. The polypeptide of claim 1, which consists of the amino acid sequence of SEQ ID NO: 1.

12. The polypeptide of claim 1, which comprises the amino acid sequence of SEQ ID NO: 3.

13. The polypeptide of claim 1, which comprises the amino acid sequence of anyone of SEQ ID NOs: 4-8 and 10-57.

14. A composition comprising a polypeptide of claim 1 and an additional biocidal agent.

15. A detergent composition comprising a surfactant and a polypeptide of claim 1.

16. An animal feed additive comprising
(a) at least one polypeptide of claim 1; and
(b) at least one fat soluble vitamin, and/or
(c) at least one water soluble vitamin, and/or
(d) at least one trace mineral, and/or
(e) at least one macro mineral.

17. The animal feed additive of claim 16, which further comprises phytase, xylanase, galactanase, and/or beta-glucanase.

18. An animal feed composition having a crude protein content of 50 to 800 g/kg and comprising at least one polypeptide of claim 1.

19. A method for killing or inhibiting growth of microbial cells comprising contacting the microbial cells with an effective amount of a polypeptide of claim 1.

20. An isolated polypeptide having antimicrobial activity, comprising the amino acid sequence of amino acids 1-19 of SEQ ID NO: 1:

```
Gly Xaa Xaa Xaa Arg Xaa Xaa Xaa Lys Ile Xaa Xaa
            5                   10

Lys Xaa Xaa Lys
        15
```

Xaa Xaa Xaa (amino acids 1-19 of SEQ ID NO: 1);
wherein
Xaa at position 2 is Leu or Arg;
Xaa at position 3 is Leu, Val, Ile or Phe;
Xaa at position 4 is Arg or Lys;
Xaa at position 6 is Leu, Val, Ile or Phe;
Xaa at position 7 is Arg, Lys, Trp or Gly;
Xaa at position 8 is Lys, Arg, Gly, Met, Asn or Glu;
Xaa at position 11 is Gly, Arg, Lys or Glu;
Xaa at position 12 is Gly, Arg, Lys or Glu;
Xaa at position 14 is Leu or Phe;
Xaa at position 15 is Lys or Arg;
Xaa at position 17 is Ile, Leu, Phe, Cys or Tyr;
Xaa at position 18 is Gly, Ala or Thr; and
Xaa at position 19 is Gln, Arg, Leu or Pro;
wherein each amino acid is independently the D or L form.

21. The polypeptide of claim 20, wherein Xaa at position 19 is Arg.

22. The polypeptide of claim 21, wherein Xaa at position 3 is Leu or Phe.

23. The polypeptide of claim 21, wherein Xaa at position 4 is Arg or Lys.

24. The polypeptide of claim 21, wherein Xaa at position 6 is Leu or Phe.

25. The polypeptide of claim 21, wherein Xaa at position 7 is Arg, Lys or Gly.

26. The polypeptide of claim 21, wherein Xaa at position 8 is Lys, Arg or Glu.

27. The polypeptide of claim 21, wherein Xaa at position 11 is Gly or Lys.

28. The polypeptide of claim 21, wherein Xaa at position 12 is Lys, Arg or Glu.

29. The polypeptide of claim 21, wherein Xaa at position 17 is Ile or Leu.

30. The polypeptide of claim 21, wherein Xaa at position 18 is Ala or Thr.

31. The polypeptide of claim 21, wherein
Xaa at position 3 is Leu or Phe;
Xaa at position 4 is Arg or Lys;
Xaa at position 6 is Leu or Phe;

Xaa at position 7 is Arg, Lys or Gly;
Xaa at position 8 is Lys, Arg or Glu;
Xaa at position 11 is Gly or Lys;
Xaa at position 12 is Lys, Arg or Glu;
Xaa at position 17 is Ile or Leu; and
Xaa at position 18 is Ala or Thr.

32. The polypeptide of claim 21, which comprises the amino acid sequence of anyone of SEQ ID NOs: 59-69.

33. A composition comprising a polypeptide of claim 21 and an additional biocidal agent.

34. A detergent composition comprising a surfactant and a polypeptide of claim 21.

35. An animal feed additive comprising
(a) at least one polypeptide of claim 21; and
(b) at least one fat soluble vitamin, and/or
(c) at least one water soluble vitamin, and/or
(d) at least one trace mineral, and/or
(e) at least one macro mineral.

36. The animal feed additive of claim 35, which further comprises phytase, xylanase, galactanase, and/or beta-glucanase.

37. An animal feed composition having a crude protein content of 50 to 800 g/kg and comprising at least one polypeptide of claim 21.

38. A method for killing or inhibiting growth of microbial cells comprising contacting the microbial cells with an effective amount of a polypeptide of claim 21.

39. The polypeptide of claim 20, which consists of the amino acid sequence of amino acids 1-19 of SEQ ID NO: 1.

40. An isolated polypeptide having antimicrobial activity, comprising the amino acid sequence of SEQ ID NO: 9.

41. A composition comprising a polypeptide of claim 40 and an additional biocidal agent.

42. A detergent composition comprising a surfactant and a polypeptide of claim 40.

43. An animal feed additive comprising
(a) at least one polypeptide of claim 40; and
(b) at least one fat soluble vitamin, and/or
(c) at least one water soluble vitamin, and/or
(d) at least one trace mineral, and/or
(e) at least one macro mineral.

44. The animal feed additive of claim 43, which further comprises phytase, xylanase, galactanase, and/or beta-glucanase.

45. An animal feed composition having a crude protein content of 50 to 800 g/kg and comprising at least one polypeptide of claim 40.

46. A method for killing or inhibiting growth of microbial cells comprising contacting the microbial cells with an effective amount of a polypeptide of claim 40.

* * * * *

UNITED STATES PATENT AND TRADEMARK OFFICE
CERTIFICATE OF CORRECTION

| | | |
|---|---|---|
| PATENT NO. | : 7,829,524 B2 | Page 1 of 1 |
| APPLICATION NO. | : 10/560260 | |
| DATED | : November 9, 2010 | |
| INVENTOR(S) | : Segura et al. | |

It is certified that error appears in the above-identified patent and that said Letters Patent is hereby corrected as shown below:

In claim 10 at column 77, line 58, delete "lie" and insert --Ile--
In claim 20, at column 78, lines 31, 33 and 40, delete "lie" and insert --Ile--

Column 80, line 26,
Please add claim 47:

47. The polypeptide of claim 20, which consists of the amino acid sequence of amino acids 1-19 of SEQ ID NO: 1.

Signed and Sealed this
Fifteenth Day of February, 2011

David J. Kappos
*Director of the United States Patent and Trademark Office*